United States Patent
Nahman et al.

(10) Patent No.: US 10,292,598 B2
(45) Date of Patent: May 21, 2019

(54) DEVICES AND METHODS FOR DETECTION OF INTERNAL BLEEDING AND HEMATOMA

(71) Applicant: Hadasit Medical Research Services and Development Ltd., Jerusalem (IL)

(72) Inventors: Dean Nahman, Jerusalem (IL); Yaron Ilan, Kefar Tavor (IL); Ilan Ben Oren, Modiin (IL); Yaron Bar-Ilan, Kfar-Tavor (IL); Shmuel Chen, Jerusalem (IL)

(73) Assignees: Dean Nahman, Jerusalem (IL); Yaron Ilan, Kefar Tavor (IL); Ilan Ben Oren, Modiin (IL); Yaron Bar-Ilan, Kfar-Tavor (IL); Shmuel Chen, Jerusalem (IL)

( * ) Notice: Subject to any disclaimer, the term of this patent is extended or adjusted under 35 U.S.C. 154(b) by 624 days.

(21) Appl. No.: 14/569,396

(22) Filed: Dec. 12, 2014

(65) Prior Publication Data
US 2015/0099980 A1    Apr. 9, 2015

Related U.S. Application Data

(63) Continuation of application No. PCT/IL2013/050509, filed on Jun. 13, 2013.
(Continued)

(51) Int. Cl.
*A61B 5/02* (2006.01)
*A61B 5/00* (2006.01)

(52) U.S. Cl.
CPC ........ *A61B 5/02042* (2013.01); *A61B 5/0075* (2013.01); *A61B 5/4875* (2013.01); *A61B 5/6833* (2013.01); *A61B 2505/05* (2013.01)

(58) Field of Classification Search
CPC .............. A61B 2505/05; A61B 5/0075; A61B 5/02042; A61B 5/4875; A61B 5/6833
See application file for complete search history.

(56) References Cited

U.S. PATENT DOCUMENTS

| 4,223,680 A | 9/1980 | Joebsis |
|---|---|---|
| 5,386,827 A | 2/1995 | Chance |

(Continued)

FOREIGN PATENT DOCUMENTS

| JP | 2009-136436 A | 6/2009 |
|---|---|---|
| WO | 96/20638 A1 | 7/1996 |

(Continued)

OTHER PUBLICATIONS

Arai et al., (1990) Infrared absorption spectra ranging from 2.5 to 10 μm at various layers of human normal abdominal aorta and fibrofatty atheroma in vitro. Lasers in Surgery and Medicine10(4): 357-362.

(Continued)

*Primary Examiner* — Michael T Rozanski
(74) *Attorney, Agent, or Firm* — Vorys, Sater, Seymour and Pease LLP

(57) ABSTRACT

A device for detection of internal bleeding in a patient's body is provided. An optical interface for transmitting IR light through an area of a skin of a patient and to collect IR light from the area of the skin, is provided. In some embodiments the optical interface includes one or more delivery components and one or more collection components. The delivery component includes a plurality of first optical channels configured to transmit the IR light through a plurality of respective first sub-areas on the area of the skin, into an internal layer of the body. The collection component includes a plurality of second optical channels,
(Continued)

configured to collect IR light from a plurality of respective second sub-areas on the area of the skin.

13 Claims, 13 Drawing Sheets

Related U.S. Application Data

(60) Provisional application No. 61/658,933, filed on Jun. 13, 2012.

(56) References Cited

U.S. PATENT DOCUMENTS

| | | | |
|---|---|---|---|
| 5,694,938 | A | 12/1997 | Feng |
| 5,954,053 | A | 9/1999 | Chance |
| 6,175,759 | B1 | 1/2001 | Chan |
| 6,233,479 | B1 | 5/2001 | Haddad |
| 6,686,582 | B1 | 2/2004 | Voelcker |
| 6,802,812 | B1 | 10/2004 | Walker |
| 6,875,176 | B2 | 4/2005 | Mourad |
| 8,060,189 | B2 | 11/2011 | Ben Dor |
| 2002/0173723 | A1 | 11/2002 | Lewis |
| 2003/0227628 | A1 | 12/2003 | Kreimer |
| 2005/0228291 | A1 | 10/2005 | Chance |
| 2006/0241495 | A1 | 10/2006 | Kurtz |
| 2006/0269972 | A1 | 11/2006 | Smith |
| 2007/0024946 | A1 | 2/2007 | Panasyuk |
| 2007/0123770 | A1 | 5/2007 | Bouton |
| 2011/0208063 | A1 | 8/2011 | Papazoglou |
| 2012/0271129 | A1 | 10/2012 | Wang |

FOREIGN PATENT DOCUMENTS

| | | |
|---|---|---|
| WO | 97/20494 A1 | 6/1997 |
| WO | 2012/092559 A1 | 7/2012 |

OTHER PUBLICATIONS

Bertrand et al., (2007) Outpatient percutaneous coronary intervention: Ready for prime time? Can J Cardiol 23 Suppl B: 58B-66B.
Chance (1998) Near-infrared images using continuous, phase-modulated, and pulsed light with quantitation of blood and blood oxygenation. Ann N Y Acad Sci 838: 29-45.
Chance et al., (1998) Phase measurement of light absorption and scatter in human tissue. Rev Sci Instrum 69(10): 3457-3481.
Chukhlantsev et al., (2003) Attenuation of electromagnetic waves by vegetation canopies in the 100-10000 MHz frequency band. Journal of Radio Electronics from: http://jre.cplire.ru/jre/feb03/4/text.html.
Doyle et al., (2008) Major femoral bleeding complications after percutaneous coronary intervention: incidence, predictors, and impact on long-term survival among 17,901 patients treated at the Mayo Clinic from 1994 to 2005. JACC Cardiovasc Intery 1(2): 202-209.
Doyle et al., (2009) Bleeding, blood transfusion, and increased mortality after percutaneous coronary intervention: implications for contemporary practice. J Am Coll Cardiol 53(22): 2019-2027.
Glaser et al., (1994) Prospective study of the incidence of ultrasound-detected hepatic hematomas due to percutaneous Menghini needle liver biopsy and laparoscopy-guided Silverman needle biopsy. Ital J Gastroenterol 26 (7): 338-341.
Hazama et al., (2008) High-energy pulsed tunable mid-infrared laser aids biomedical applications. SPIE Newsroom; 3 pages.
Hofmann et al., (2011) A novel approach to non-invasive blood glucose measurement based on RF transmission. Medical Measurements and Applications Proceedings (MeMeA), 2011 IEEE International Workshop on, Bari, Italy pp. 39-42.
Klonoff et al., (1998) Mid-Infrared Spectroscopy for Noninvasive Blood Glucose Monitoring. IEEE LEOS Newsletter 12: 13-14.
Malvasi et al., (2008) Subfascial hematomas and hemoperitoneum after cesarean section: prevalence according to closure and non-closure of the parietal peritoneum. Gynecol Obstet Invest 66(3): 162-168.
McCrea et al., (2008) The diagnosis, management, and postnatal prevention of intraventricular hemorrhage in the preterm neonate. Clin Perinatol 35(4): 777-792.
Pleshko et al., Optical Spectroscopy of Engineered Connective Tissues: Mapping Molecular Components. 17th Annual ISMRM Scientific Meeting and Exhibition 2009, Honolulu, Hawaii, USA Apr. 18-24, 2009, 3 pages.
Shaw et al., (2008) Infrared spectroscopy in clinical and diagnostic analysis. In: Encyclopedia of Analytical Chemistry, edited by Robert A. Meyers, John Wiley & Sons Ltd, Chichester, pp. 1-20.
Smith et al., (1985) Dielectric properties of low-water-content tissues. Phys Med Biol 30(9): 965-973.
Traille et al., (2011) Liquid RF antennas, electronics and sensors: A modeling challenge. General Assembly and Scientific Symposium, 2011 XXXth URSI, Istanbul, Turkey, Aug. 13-20, 2011, 4 pages.
Werber et al., (2006) Investigation of RF transmission properties of human tissues. Advances in Radio Science 4: 357-360.
Zhang et al., (2000) Brain perfusion monitoring with frequency-domain and continuous-wave near-infrared Spectroscopy: a cross-correlation study in newborn piglets. Phys Med Biol 45(11): 3143-3158.

DEVICES AND METHODS FOR DETECTION OF INTERNAL BLEEDING AND HEMATOMA

This application is a § 371 of PCT Application PCT/IL2013/050509, filed on 13 Jun. 2013, which claims benefit from U.S. Provisional Application Ser. No. 61/658,933 filed on 13 Jun. 2012 all of which are incorporated by reference as if fully set forth herein.

FIELD OF THE INVENTION

The present invention relates to devices and methods for detection of internal bleeding and hematoma.

BACKGROUND OF THE INVENTION

Internal bleeding (also known as internal hemorrhage), namely the leaking of blood from the vascular system into body cavities or spaces, is a major, potentially life-threatening complication associated with invasive medical procedures.

Examples of invasive and minimally invasive medical procedures that are associated with a profound risk of internal bleeding include coronary angiography and catheterization, percutaneous coronary intervention, a caesarean section, percutaneous biopsies (e.g. liver, kidney, lung), laparoscopic procedures and coronary artery bypass grafting.

Post-operative surgical site bleeding is another major cause of concern. Intra peritoneal bleeding after an abdominal surgery may lead to unnoticed hypo-volemic shock. Pericardial bleeding after cardiac surgery may lead to space occupying hematoma and pericardial tamponade.

Internal bleeding may also occur as a result of internal trauma and injuries of the human body. Internal bleeding may also result from medical conditions associated with an increased risk of bleeding. For example, a medical condition in which development of internal bleeding is a serious risk is a cranial intra-ventricular hemorrhage (IVH) in premature neonates. Several studies estimated that the risk for IVH in very low birth weight neonates is 20-25%; many of these will suffer severe neurodevelopmental sequelae. Early diagnosis of IVH may allow early treatment and late disability prevention.

Diagnosis of internal bleeding is often problematic, since symptoms may not be evident until a significant amount of blood is lost and/or a blood clot is formed that is large enough to press adjacent organs and disrupt their proper functioning. Furthermore, after medical procedures, most patients suffer physical pain and blurred awareness which overcome the sings of internal bleeding. In addition to internal bleeding, invasive procedures may lead to additional changes to the body tissues at the operation area, including for example edema, which may complicate the detection and correct diagnosis of bleeding and hematoma. Early detection of internal bleeding is desired, as it may facilitate optimal treatment and prevention of mortality.

Hemoglobin in red blood cells absorbs near infra-red (NIR) light. Extra-vascular blood is more concentrated compared to intra-vascular, thus absorbing more NIR light. Several blood analytes, including for example urea, triglycerides, cholesterol, glucose, total protein and albumin, are known to absorb mid infra-red (MIR) light. MIR at certain wavelengths is generally not absorbed by the surrounding tissue (Shaw and Mantsch 2008 "Infrared spectroscopy in clinical and diagnostic analysis"; In: *Encyclopedia of Analytical Chemistry*, edited by Robert A. Meyers, John Wiley & Sons Ltd, Chichester, pp. 1-19; Klonoff et al. 1998 *IEEE Photonics Society*, vol. 12(2) April Newsletter; Hazama et al. 2008 "High-energy pulsed tunable mid-infrared laser aids biomedical applications", SPIE Newsroom; and Arai et al. 1990 "infrared absorption spectra ranging from 2.5 to 10 μm at various layers of human normal abdominal aorta and fibrofatty atheroma in vitro", *Lasers in Surgery and Medicine*, 10(4); 357-362).

Water content in body tissues affects dielectric properties of the tissues, reflected in their varying interaction with radio-frequency (RF) radiation (Werber et al. 2006 "Investigation of RF transmission properties of human tissues", *Advances in Radio Science*, 4: 357-360; Smith et al. 1985 "Dielectric properties of low-water-content tissues" *Phys Med Biol.* 30(9):965-73; and Hofmann et al. 2011 *Proc. IEEE Int. Symp. Medical Meas. Applications*, Bari, Italy, pp. 39-42).

U.S. Pat. No. 5,694,938 discloses non-invasive near infrared optical medical imaging devices for both hematoma detection in the brain and early tumor detection in the breast. This is achieved using image reconstruction which allows a mapping of the position dependent contrast diffusive propagation constants, which are related to the optical absorption coefficient and scattering coefficient in the tissue, at near infrared wavelengths.

U.S. Pat. No. 5,954,053 is directed, inter alia, to detection of brain hematoma and discloses systems that utilize differential measurement of radiation that has migrated through migration paths between two source-detector pairs placed on the head in a manner that each path is localized in a portion of one hemisphere of the brain.

U.S. Pat. No. 6,175,759 discloses a non-invasive multi-spectral energy system made up of a transilluminating radiating means that illuminates soft tissues that have been treated with a contrast agent using first and second near-IR illuminating signals to produce thereby a first and second near-IR multispectral images; means for optically combining the first and second near-IR multispectral images into a combined tissue image; and a means for processing the combined tissue image to detect cancer and tumors and internal bleeding.

U.S. Pat. No. 6,233,479 discloses a non-invasive device designed to detect and localize blood pooling and clots near the outer surface of the body. While being geared towards finding sub-dural and epi-dural hematomas, the device can be used to detect blood pooling anywhere near the surface of the body. The device is based on low power pulsed microwave technology combined with a specialized antenna, signal processing/recognition algorithms and a disposable cap worn by the patient which will facilitate accurate mapping of the brain and proper function of the instrument.

U.S. Pat. No. 6,875,176 discloses systems and methods for assessment of tissue properties, noninvasively, by acquiring data relating to at least one aspect of intrinsic and/or induced tissue displacement, or associated biological responses. Data relating to tissue displacement and associated biological changes may be acquired by detecting acoustic properties of tissue using ultrasound interrogation pulses, preferably in a scatter or Doppler detection mode. In some embodiments, detection techniques, including near-infrared spectroscopy (NIRS), magnetic resonance techniques, acoustic hydrophones and the like, are also used.

US 2009/0221919 (now U.S. Pat. No. 8,060,189) discloses, inter alia, a device for intra cranial hematoma detection, in head trauma settings, using the differences in NIR light absorbance between the two cranial hemispheres that may appear when blood accumulates in one cranial hemisphere.

JP 2009136436 discloses an internal hemorrhage detecting apparatus comprising an armrest for placing an arm, a near infrared LED for irradiating the arm rested on the armrest with near infrared rays, and a near infrared camera for continuously imaging a position of the arm to which the near infrared rays are applied. An analysis range is extracted from a comparison image captured by the near infrared camera, and the area of the position where the luminance is lower than a prescribed threshold is found. Blood is determined to be present in other regions than veins if the area is increased by a prescribed quantity.

There is still a need in the art for devices, systems and methods for early detection of internal bleeding and hematoma formation in body parts of interest, particularly following invasive procedures. For example, it would be highly beneficial to have devices, systems and methods for non-invasively monitoring a patient following an invasive procedure in order to detect internal bleeding as early as possible after it begins, while distinguishing between bleeding and other changes to tissues, such as formation of edema.

SUMMARY OF THE INVENTION

The present invention in embodiments thereof provides devices and methods for non-invasive detection of internal bleeding and hematoma formation within an internal body part of a patient. The devices and methods disclosed herein, in some embodiments, deliver and collect Infra-Red (IR) light having a wavelength absorbed substantially exclusively by blood, for example near-IR absorbed substantially exclusively by hemoglobin, to and from an internal body part of a patient, through an area on the skin of the patient. In some embodiments, the devices and methods further deliver and collect a reference signal having a wavelength which is not absorbed substantially exclusively by blood, to and from the internal body part of a patient, through substantially the same area on the skin of the patient. According to some embodiments, the devices and methods track and detect changes, such as temporal changes, in parameters of the two signals as collected from the skin area, thereby detecting bleeding while filtering noise and differentiating between bleeding and other changes to tissues, such as edema formation.

As used herein, "internal bleeding" refers to the leaking of blood from blood vessels into spaces and cavities within the body. The term "internal" indicates that the bleeding is generally not visible when looking at the patient from the outside. The patient according to embodiments of the present invention is a subject, including but not limited to a human subject, at risk of developing an internal bleeding. In some embodiments, the patient is a subject who has undergone an invasive or minimally invasive medical procedure or surgical intervention. In additional embodiments, the patient is a subject suffering from a medical condition associated with an increased risk of internal bleeding. The patient according to embodiments of the present invention is in need of monitoring of internal bleeding, if occurs, preferably as early as possible after it begins. In some embodiments, there is a need to monitor the patient over a relatively long period of time, as bleeding may develop several hours, or several dozens of hours following an invasive procedure. In addition, there is a need for a sensitive yet specific detection of bleeding, as invasive or minimally invasive medical procedures may cause changes to body tissues in the operation area, as well as in areas adjacent to the operation area, which are not associated with bleeding. For example, in addition to the risk of bleeding and accumulation of blood in internal body cavities, interstitial fluids may accumulate and form edema. Such changes may affect the interaction of the tissues with electromagnetic radiation, as employed by the devices and methods of the present invention. Thus, there is a need to filter out the effects of changes not associated with bleeding on collected signals and differentiate between variation of signals collected from the body due to bleeding and variation due to other changes not associated with bleeding.

In order to meet the above needs, the devices of the present invention, according to some embodiments, conduct continuous monitoring, and integrate data collected over a period of time in order to identify changes and variations in the signals. In addition, the devices of the present invention, in some embodiments, employ a reference signal in order to differentiate between changes in the main signal that are due to bleeding and changes in the main signal due to other causes, such as accumulation of fluids other than blood. In addition, the devices of the present invention, in some embodiments, are configured such that they cover a large area where bleeding may occur. In some embodiments, the devices comprise a plurality of channels, each covers a sub-area within the tested area, and the plurality of channels collectively covers a broad area, thereby facilitating the detection of internal bleeding.

Advantageously, the devices of the present invention, according to some embodiments, enable delivery of IR and reference signals to deep layers of the body, for example to a depth of about 2 cm or more, 5 cm or more, 10 cm or more from the surface of the skin, as well as collection of signals reflected from such deep layers, where internal bleeding may occur.

By employing a plurality of substantially separated channels, the devices of the present invention enable, in some embodiments, identifying the locality of the bleeding within the internal body part. Thus, in some embodiments, the devices of the present invention provide an indication regarding a particular location of the detected bleeding within an internal body part of a patient.

In some embodiments, the devices are employed for the detection of internal bleeding within a limb, abdominal cavity, chest cavity or digestive tract.

According to an aspect of some embodiments there is provided a device for detection of internal bleeding in a patient's body, the device comprises: an IR light source configured to generate light in the Infra-Red (IR) spectral range; an IR light detector configured to detect light in the Infra-Red (IR) spectral range; an optical interface comprising one or more delivery component comprising at least one first optical channel, and configured to deliver IR light generated by said IR light source and to transmit said IR light through an at least one respective first sub-area, on an area of a skin of said patient, into an internal layer of the body, and one or more collection component comprising at least one second optical channel, configured to collect IR light from an at least one respective second sub-area, on said area of said skin, and deliver said collected IR light to said IR light detector; a reference signal source configured to generate a reference signal and a reference signal detector configured to detect said reference signal and a reference signal interface configured to deliver through the skin of the patient a reference signal from said reference signal source into said internal layer and to collect and deliver a collected reference signal to said reference signal detector, wherein an IR light detected by said IR detector has a wavelength λ1 and a reference signal detected by said reference signal detector has wavelength λ2 substantially different from λ1; and a signal processing module comprising a processor configured to compare measurement results of detected IR light, detected by said IR detector, and measurement results of detected reference signal, detected by said reference signal detector, thereby detecting an internal bleeding in a patient's body.

According to an aspect of some embodiments there is provided an optical interface for transmitting IR light to an area of a skin of a patient and to collect IR light from said area of the skin, configured to be attached to the patient's body at said area or proximal thereto and comprising: one or more delivery component, comprising a plurality of first optical channels configured to transmit said IR light through a plurality of respective first sub-areas, on said area of the skin, into an internal layer of the body; and one or more collection component, comprising a plurality of second optical channels, configured to collect IR light from a plurality of respective second sub-areas on said area of the skin.

According to an aspect of some embodiments there is provided a method for detecting internal bleeding in a patient's body, comprising: providing the device of any one of the preceding claims; transmitting IR light at a sub area on an area of a skin of said patient, into an internal layer of the body; collecting and detecting IR light scattered from a sub-area on the area of the skin; delivering a reference signal through the skin of said patient, into said internal layer of the body; collecting and detecting said reference signal from said body of the patient, and comparing measurement results of said detected IR light and measurement results of said detected reference signal.

According to an aspect of some embodiments there is provided a method for detecting internal bleeding in a patient's body, comprising: measuring detected IR light, IBL, associated with absorption in blood, at a first point in time t=0; measuring detected reference signal, RefBL, at t=0; establishing (calculating) a normalized signal SBL=IBL/RefBL; measuring detected IR light, IT, associated with absorption in blood, at a later point in time t=T; measuring detected reference signal, RefT, at t=T; establishing (calculating) a normalized signal ST=IT/RefT; comparing ST to SBL; if the comparison in the previous step indicates detection of bleeding, activating an alarm; and returning to the steps of measuring detected IR light, IT, and measuring detected reference signal, RefT, at yet a later point in time.

These and further aspects and features of the present invention will become apparent from the figures, detailed description and claims which follow.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION OF THE INVENTION

The present invention relates to devices and methods for detection of internal bleeding in a body part of a patient.

Figure 1:
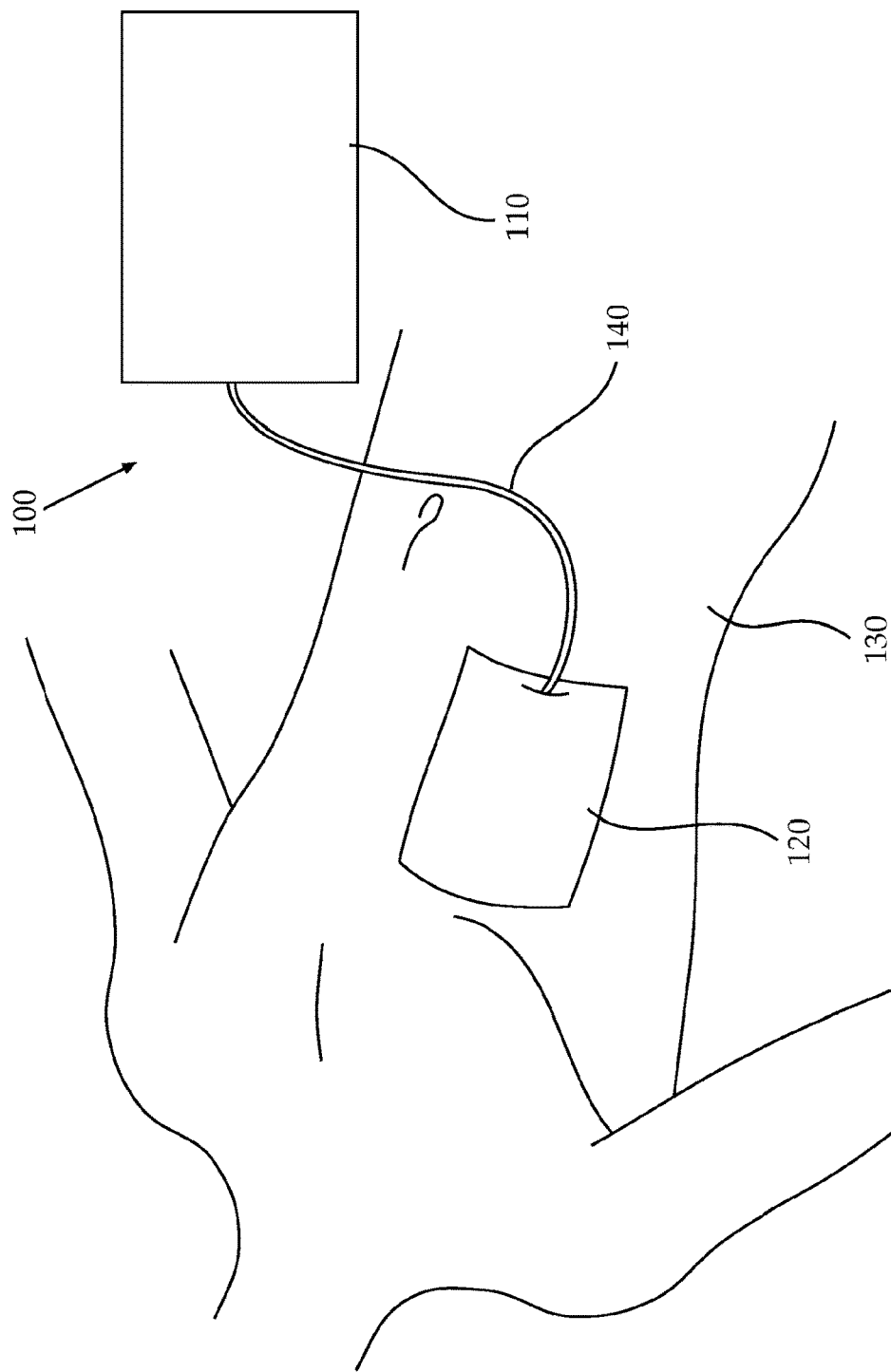
FIG. 1 schematically depicts a device for detection of internal bleeding according to exemplary embodiments of the current invention.

Reference is now made to FIG. 1 which schematically depicts a device for detection of internal bleeding according to exemplary embodiments of the current invention. The device (100) includes a control unit (110) and an optic interface (120) comprising an adhesive pad and attached to a patient's body (130).

The control unit may include a signal processing module comprising a processor configured to analyze data collected from the patient. The control unit may include a user interface such as keyboard, mouse, display, switches and/or operating knobs. The control unit is associated with the optical interface and allows a user to activate the device. In the illustrated embodiment, a wire (140) connects between the control unit and the optic interface. In some embodiments, one or more optic fibers connect between the control unit and the optic interface. In some embodiments, the control unit comprises signal sources and detectors. In other embodiments, signal sources and detectors are included within the optic interface unit that is attached to the patient's skin. The optic interface typically comprises delivery components and collection components for delivering and collecting signals to and from the skin of the patient.

Figure 2:
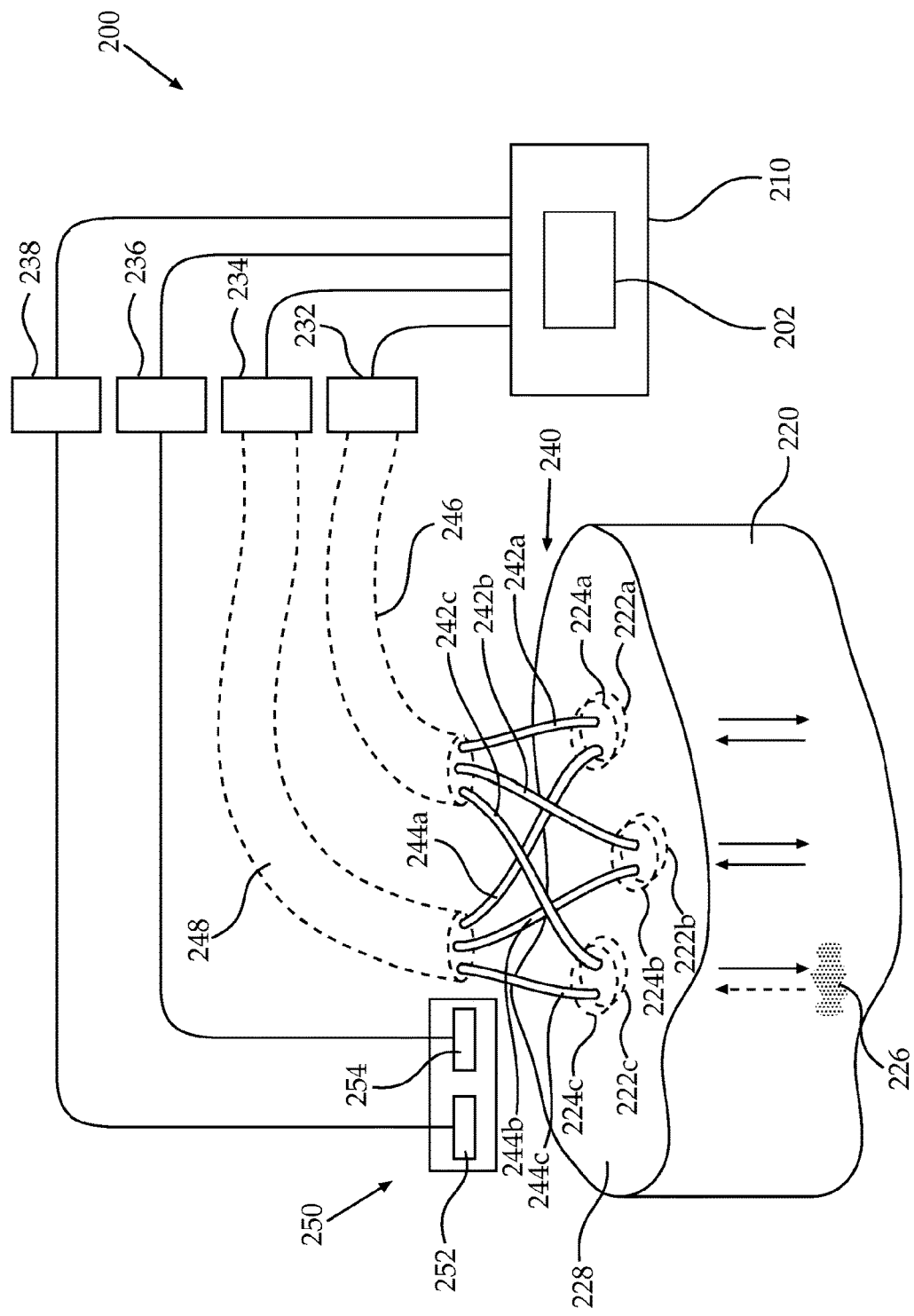
FIG. 2 schematically depicts a device for detection of internal bleeding according to some exemplary embodiments of the current invention.

Reference is now made to FIG. 2, which schematically depicts a device for detection of internal bleeding according to some exemplary embodiments of the current invention, in association with a body part to be scanned or monitored for the presence of bleeding or hematoma. The illustrated device (200) includes a signal processing module (210) comprising a processor (202), an Infra-Red (IR) light source (232) and a reference signal source (238). The IR light source and/or the reference signal source may be LED(s) or laser(s), such as a diode laser. The IR light source is configured to generate light in the IR spectral range at one or more wavelengths $\lambda s$, absorbed substantially exclusively by blood. For example The IR light source is configured to generate IR light that is absorbed by hemoglobin. For example, The IR light source is configured to generate IR light having a wavelength including but not limited to, about 760 nm, about 780 nm, about 830 nm and/or about 850 nm or any combination thereof. Alternatively, the IR light source is configured to generate a wide-spectrum light having a spectral width selected from the group consisting of about 30, 50, 100 and 200 nm within the IR spectral range. The reference signal source is configured to generate a reference signal having a wavelength not absorbed by hemoglobin. The illustrated device further includes an IR light detector (234) and a reference signal detector (236). The IR light detector and/or the reference signal detector may be CCD and/or CMOS.

The illustrated device further includes an optical interface (240). The illustrated optical interface comprises a delivery component (246) configured to deliver the IR light generated by the IR light source and transmit it at an area of the skin of the patient (228), into an internal layer of the patient's body (220). The device according to embodiments of the present invention typically covers a skin area of about $2\times2\text{-}10\times10$ cm$^2$, for example about $2\times2\text{-}5\times5$ cm$^2$. The light is typically transmitted into an internal layer of the patient's body, to a depth of about 0-10 cm, for example about 0-1 cm, about 1-10 cm, about 2-10 cm. The illustrated delivery component comprises a plurality of optical channels (for example, an array of three optical channels (242$a,b,c$) as in the illustrated embodiment). According to some embodiments the delivery component comprises optic fibers, each fiber is configured to transmit light at a location, or sub-area (222,$a,b$ or $c$), within the skin area. According to some embodiments the delivery component comprises a lens (not shown in the figure) through which IR light is transmitted to the sub area. In some embodiments the delivery component comprises an optically neutral component such as a transparent window through which IR light is transmitted to the sub area.

The illustrated optical interface further includes a collection component (248) configured to collect IR light from sub-areas (224$a,b,c$) within the skin area, which in this example have only partial overlap with the sub-areas (222$a,b,c$) at which IR light is delivered by the delivery component. Thus, in this example, the optic channels of the delivery component are configured to transmit light at a first plurality of sub-areas within the skin area, and the optic channels of the collection component are configured to collect light from a second plurality of sub-areas within the skin area.

The collection component is further configured to deliver the collected light to the IR light detector. Similar to the illustrated delivery component, the illustrated collection component comprises a plurality of optical channels (for example, an array of three optical channels (244,$a,b,c$) as in the illustrated embodiment). In some embodiments, the collection component comprises optic fibers, each fiber is configured to collect light from a location, or sub-area, within the skin area. In some embodiments, the collection component comprises a lens (not shown in the figure) through which IR light is collected from sub area. In some embodiments the collection component comprises an optically neutral component such as a transparent window through which IR light is collected from the sub area.

The reference signal source (238) is configured to generate a reference signal having a wavelength $\lambda\text{ref}$, different from $\lambda s$, which is not absorbed substantially exclusively by blood. According to some embodiments, the reference signal is selected so as to be absorbed by water. According to some embodiments, the reference signal is selected so as to be absorbed by interstitial fluid. According to some embodiments, the reference signal is selected to be absorbed substantially similarly by blood and by any liquid that may accumulate in body tissue following a surgical intervention, such as interstitial fluid.

According to some embodiments the illustrated device comprises a reference signal source configured to generate a reference signal as described above. The illustrated device further comprises a reference signal detector configured to detect the reference signal. The illustrated device further comprises a reference signal interface (250), configured to deliver through the skin of the patient a reference signal from the reference signal source into the internal layer, and to collect and deliver a collected reference signal to the reference signal detector.

Thus, according to some embodiments the reference signal is a NIR signal having a wavelength not selectively absorbed by hemoglobin. According to some embodiments the reference signal is a Mid-IR signal having a wavelength not selectively absorbed by hemoglobin. According to some embodiments the reference signal is a radio-frequency (RF) signal having a wavelength not selectively absorbed by hemoglobin. By "not selectively absorbed" it is meant that a signal at that wavelength and signals at neighboring wavelengths are substantially similarly absorbed (e.g. by hemoglobin).

According to some embodiments a NIR light source is used a source for the NIR light as described above and also as a reference signal source. In some embodiments the NIR light source is configured to generate a NIR signal comprising continuously substantially two or more discrete wavelengths, or a wide spectrum NIR signal wherein one or more wavelengths are substantially exclusively absorbed by blood, e.g. by hemoglobin, and the other wavelengths are absorbed substantially similarly by blood and by other body liquids such as water or interstitial fluid. Further, NIR light collected from the area of the skin by the collection component is filtered so that a spectral component comprising $\lambda s$, selectively absorbed by blood, is delivered to the IR light detector. The NIR light collected from the area of the skin by the collection component is also filtered so that a spectral component not comprising $\lambda s$ is delivered to the reference signal detector. In such embodiments, the NIR light source is used also as a reference signal source, and the optical interface is used also as the reference signal interface.

According to some embodiments the NIR light source is configured to generate a NIR light having a time-varying wavelength according to a pre-defined variation scheme, e.g. by continuous scanning of a wavelength range or by generating a NIR signal at substantially two or more alternating discrete wavelengths. In such embodiments the NIR light source may be used also as a reference signal source, the optical interface unit may used also as the reference signal interface unit, and the NIR detector may be used also as a reference signal detector. In such embodiments the transmitted NIR light is substantially exclusively absorbed in blood at specific points in time, defined by the wavelength variation scheme of the light, whereas at other points in time it is not substantially exclusively absorbed in blood, thereby being fit to be used as a reference signal. Thus, according to the wavelength variation scheme of the light, measurement results of the detected NIR light at some points in time are considered as a signal indicative of presence of blood in the internal layer of the body, whereas measurement results of the detected NIR light at other points in time are considered as a reference signal.

The illustrated device further comprises a signal processing module (210) comprising a processor (202). According to some embodiments the signal processing module is configured to control the IR light source and the IR light detector, the reference signal source and the reference signal detector. The signal processing module is further configured to obtain measurement results of the detected IR light and of the detected reference signal. Such measurement results may include measurement of parameters such as magnitude, amplitude, power, spectral line width, spectral content and spectral distribution of power. The processor is configured to compare results of measured parameters of the detected IR light, to measurement results of measured parameters of the detected reference signal. According to some embodiments, the processor is further configured to obtain a time-dependent sequence of such measurement results and it may further obtain desired functions of the results or mathematical manipulations thereof or desired calculations using such results, as is further detailed herein.

According to some embodiments the signal processing module is configured to controllably modulate the IR light generated by the IR light source, so that the associated optical channels deliver modulated IR light to the skin of the patient. The processing module may controllably modulate the IR light e.g. by providing a modulating signal directly to the IR light source or, according to some embodiments, by providing a modulating signal to a modulating device (not shown in this figure) in the optic channels of the delivery component. According to some embodiments the signal processing module is further configured to modulate the collected IR light synchronously with the modulation of generated IR light. According to some embodiments the signal processing module may employ known techniques of matched filtering to the detected IR light, using the modulation of the transmitted IR light and/or the modulation of the detected IR light, to enhance the signal-to-noise ratio (SNR) of the measurements.

In some embodiments, the optical interface is configured to be attached to the skin of the patient. In some embodiments, the optical interface comprises an adhesive pad for attaching the optical interface to the skin of the patient. In some embodiments, the device comprises an adhesive pad housing the optical interface and configured for attaching the optical interface to the skin of the patient.

It is to be understood that every part of the device can be designed for single or multiple uses. For example, an optical interface configured to be attached to the skin of the patient in the form of a pad may be configured for single use (disposable). The pad may be flexible. The pad may include a series of lenses, such as micro-lenses, and/or means for coupling optical fibers.

As illustrated in the figure, the tested body part (220) contains a hematoma (226) below sub-areas 222c and 224c. As further illustrated in the figure, light (marked by arrows) is delivered to and from the internal body part. The light collected from the hematoma area (dashed line) differ in its parameters from light collected from the adjacent areas (solid lines), and this difference will be identified by analysis of the signals collected from the skin. In some embodiments, different spectrum of diffusive reflection is obtained from the hematoma area, due to accumulation of hemoglobin in hematoma as compared to flowing blood.

Figure 3:
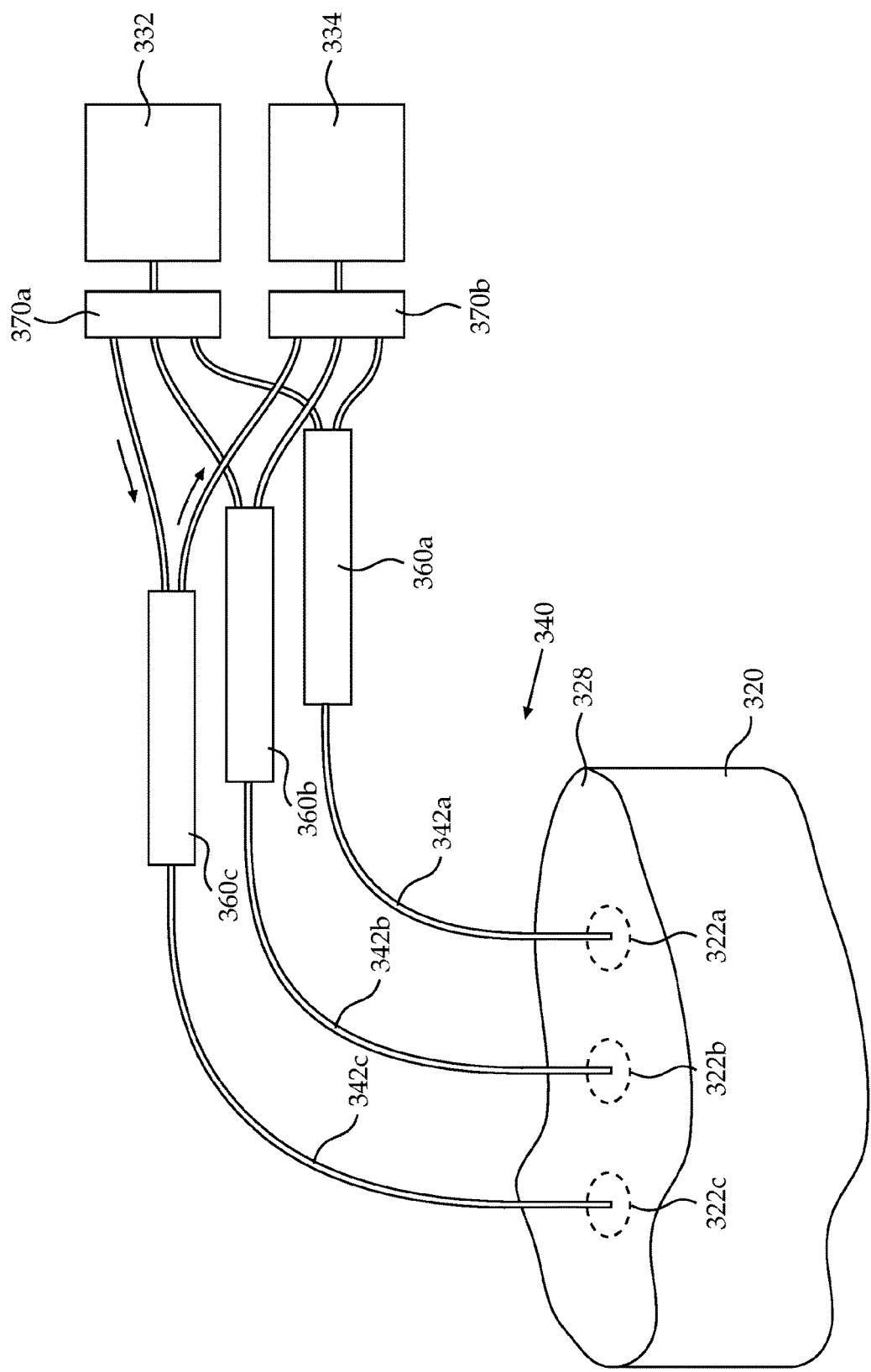
FIG. 3 schematically depicts a configuration of components within a device for detection of internal bleeding according to an exemplary embodiment of the current invention.

Reference is now made to FIG. 3, which schematically depicts a configuration of components within a device for detection of internal bleeding according to an exemplary embodiment of the current invention. Further shown is a body part to be scanned for the presence of bleeding or hematoma. The configuration shown in FIG. 3 is based on fibers and fiber optic splitter (beam splitter).

The illustrated configuration includes a light source (332), a light detector (334) and an optical interface (340) comprising a plurality of optic fibers (three optic fibers, 342a, b,c) for the delivery of light generated by the light source to a plurality of sub-areas (322a,b,c) within a skin area (328) and into an internal layer of the body part (320), and light collected from the plurality of sub-areas of the skin to the light detector. In this example, the delivery and collection of light to and from a particular sub-area is performed through the same optical channel, namely by a single optic fiber. In the illustrated embodiment, a plurality of beam splitters (three beam splitters 360a,b,c), one for each optic fiber, is functionally disposed between the optical interface comprising the fibers, and the light source and detector. In other embodiments, the beam splitters may be included within the optical interface. Each beam splitter is configured to deliver light from the light source to its respective optic fiber, and to deliver light from the respective optic fiber to the light detector. A first spatial light modulator (370a) is functionally disposed between the plurality of beam splitters and the light source, the first spatial light modulator is configured to controllably and selectively deliver light from the light source to each of the plurality of beam splitters. A second spatial light modulator (370b) is functionally disposed between the plurality of beam splitters and the light detector, the second spatial light modulator is configured to controllably and selectively deliver light from each of the plurality of beam splitters to the light detector. In some embodiments, the one or more of the spatial light modulators can be included within the optical interface unit.

Figure 4B:
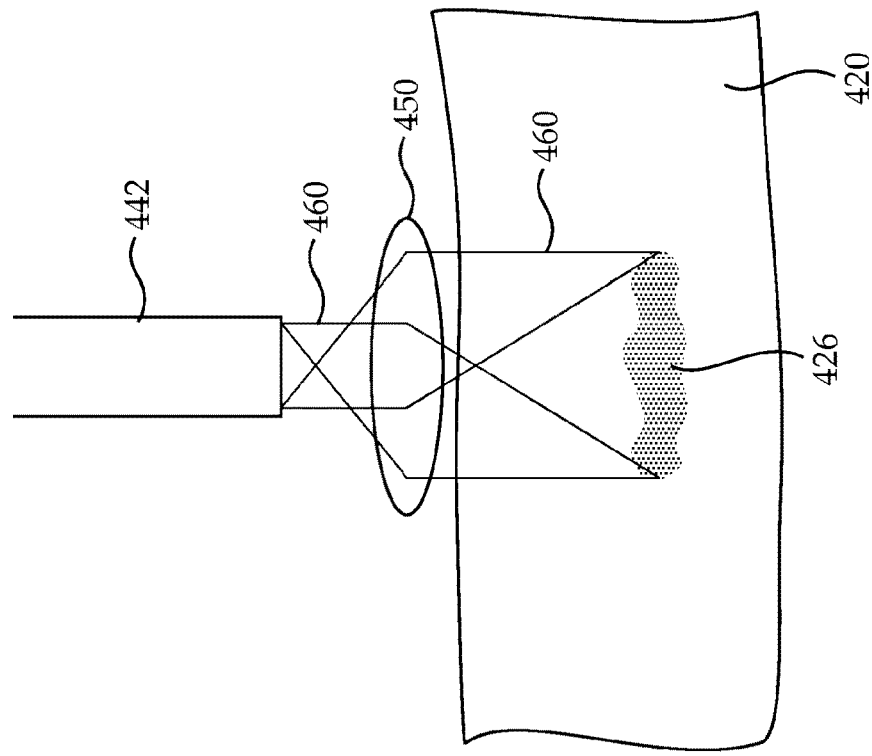
FIGS. 4A-4B schematically depict configurations of optical fibers for use in an optical interface in devices for detection of bleeding according to exemplary embodiments of the current invention.
Figure 4A:
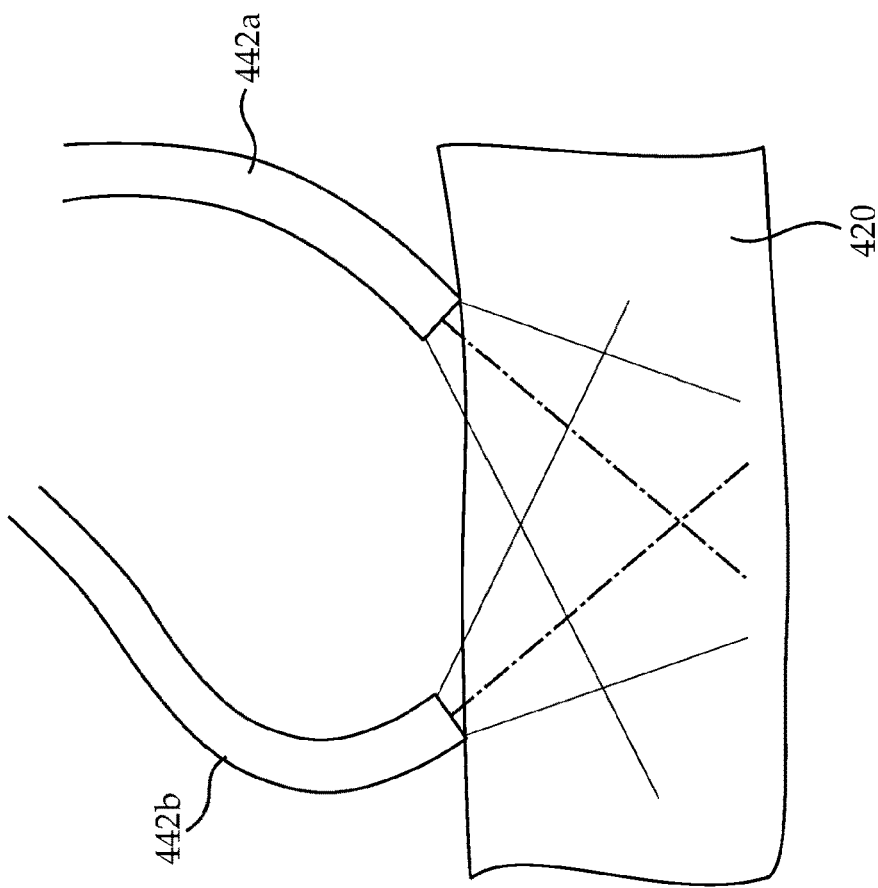

Reference is now made to FIGS. 4A-B, which schematically depict configurations of optical fibers for use in an optical interface in devices for detection of bleeding according to exemplary embodiments of the current invention The configuration shown in FIG. 4A is based on a dual fiber assembly (442a,b) which may help diagnosing internal bleeding by a simplified method wherein minimal optics is used to deliver the light into the tissue from the fiber exit and to collect the back reflected light. The light transmitted to the tissue (420) is configured to enter the body surface at an angle lower than 90°, such as about 45°. This configuration increases the amount of scattered light that reaches the detector and also enables larger area coverage.

In some embodiments employing this configuration, the illumination and light collection is done with channels that are not perpendicular to the skin surface area. Light from one channel is scattered and reflected and collected also by neighbor channels. In accordance with this embodiment, light emitted from channel "n" is scattered by the tissue and collected by the neighboring channels and similarly channel "n" collects not just the light back-emitted from itself but from neighboring channels as well.

According to some embodiments such configuration may employ a dual fiber assembly essentially without further optics. The fibers used have a large core diameter and a large numerical aperture, therefore no optics for manipulation of light from the fiber and for collection is necessary.

Reference is now made to FIG. 4B, depicting schematically an optical fiber (442) and an optically associated lens (450), configured to transmit IR light (460) through the skin into an internal layer of a body (420). The optical fiber and the lens are further optically configured for optimized collection of IR light scattered from internal layers of the body, thereby enabling or facilitating detecting bleeding in layers of the body that are as deep as a few centimeters—e.g. 5 cm or 7 cm or even 10 cm—inside the body. According to the illustrated embodiment the lens focuses the light beam that emerges from the optical fiber to allow a transmitted beam angle as small as 2-5 degrees, instead of a beam angle of 10-20 degrees typical to an optical fiber without a lens. Moreover, the lens, having a diameter significantly larger than the core diameter of the fiber, is configured to collect light from a region inside the body (426) having a larger cross-section and smaller opening angle, relative to the region from which light may be collected using a fiber without a lens.

Figure 5:
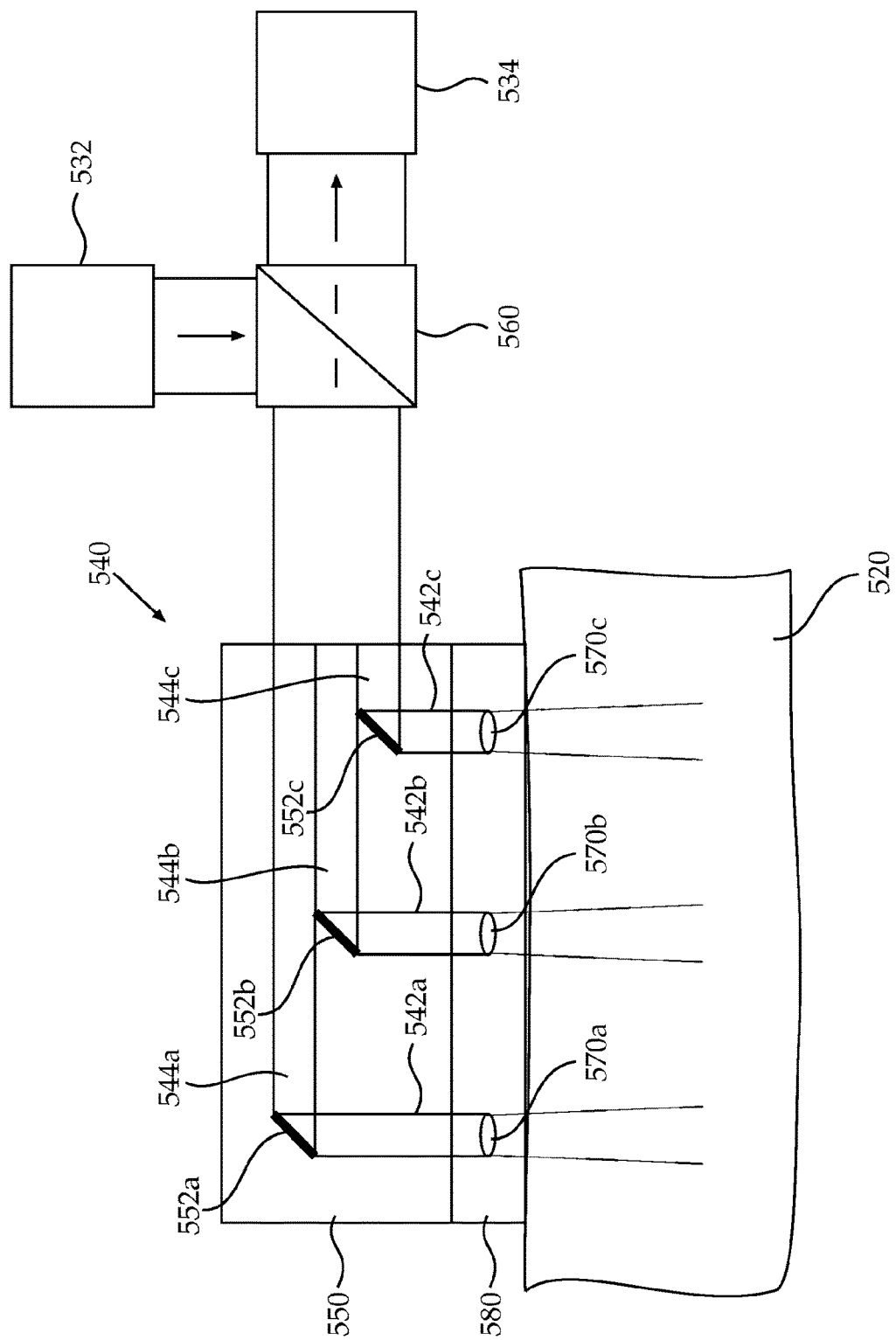
FIG. 5 schematically depicts a configuration of components within a device for detection of internal bleeding according to an exemplary embodiment of the current invention.

Reference is now made to FIG. 5, which schematically depicts a configuration of components within a device for detection of internal bleeding according to an exemplary embodiment of the current invention. In this configuration, a waveguide assembly (550) comprising mirrors (552a,b,c) and lenses (570a,b,c) is used for the delivery and collection of light to and from the skin of the patient. In some embodiments, the waveguide comprises an adhesive part (580) configured to attach the waveguide assembly to the skin of the patient. The adhesive part may be an integral part of the waveguide assembly or the waveguide assembly itself may be adhesive. The illustrated configuration includes a light source (532), a light detector (534) and an optical interface (540) comprising a waveguide assembly. A beam splitter (560) is functionally disposed between the waveguide assembly, and the light source and detector. The beam splitter is configured to deliver light from the light source to the waveguide assembly, and to deliver light from the waveguide assembly to the light detector. The illustrated waveguide assembly comprises a plurality of optical channels (542a,b,c), each optical channel is configured to deliver light to and from a sub-area within a skin area of the patient. The waveguide can be built with one or more reflective elements, such as mirrors (552a,b,c), as shown in the figure. In the illustrated embodiment, the mirrors are partial/small mirrors arranged such that they are spatially separated across the waveguide. More specifically, the mirrors are arranged at different distances from the point in which light from the beam splitter enters the waveguide, and at different heights within the waveguide. Each mirror is configured to receive light from the beam splitter and deflect light towards a sub-area within an area of a skin of the patient, and into an internal part of the body of the patient. Each mirror is further configured to receive light from that sub-area and deflect the light towards the beam splitter. The spatial division of the mirrors within the waveguide creates a plurality of optical channels that are spatially distinct thus allowing spatial resolution of the signals delivered and collected from the skin area covered. Spatial resolution of the signals is maintained both when the signals are delivered to the skin and when collected from the skin. In some embodiments, each mirror is optically associated with a respective lens (570a,b,c), such as a mini- or micro-lens, for the delivery and collection of light towards and from the skin sub-area. In some embodiments, the waveguide assembly further comprises a plurality of optic fibers (544a,b,c), each is configured to deliver light to and from a sub-area within the skin area. In some embodiments, an array of optic fibers is used, where the fibers are spatially separated to maintain spatial resolution of the delivered and collected signals. For example, the optic fibers may be arranged at different heights within the waveguide. Each optic fiber may be optically associated with a respective mirror and optionally with a respective lens, to direct light towards a sub-area within the skin area, and collect light from the sub-area.

Figure 6:
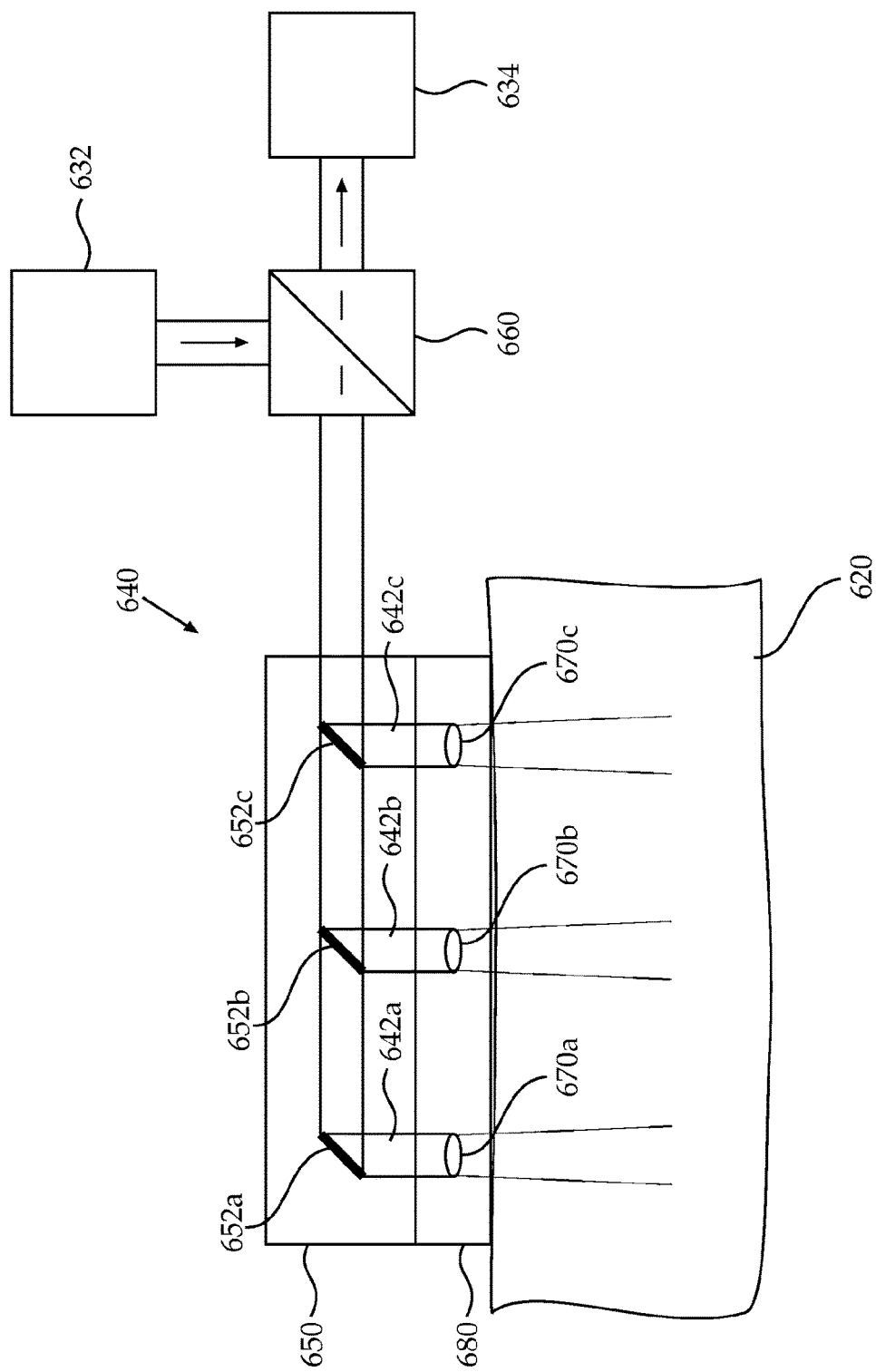
FIG. 6 schematically depicts a configuration of components within a device for detection of internal bleeding according to an exemplary embodiment of the current invention.

Reference is now made to FIG. 6, which schematically depicts a configuration of components within a device for detection of internal bleeding according to an exemplary embodiment of the current invention. Similar to FIG. 5, a waveguide assembly (650) comprising mirrors (652a,b,c) and lenses (670a,b,c), such as mini- or micro-lenses, is used to deliver light to and from an area of the skin of the patient. In the illustrated embodiment, the mirrors are semi-reflective/semi-transparent mirrors, arranged at different distances from the point in which light from the beam splitter (660) enters the waveguide, at the same height within the waveguide. This configuration enables delivery of light to a plurality of sub-areas within an area of the skin of the subject. Each mirror is configured to reflect light towards a sub-area within an area of the skin of the subject, receive light from that sub-area and reflect the light towards the beam splitter. Each mirror is further configured to transmit a portion of the light received by the mirror to an adjacent mirror. In some embodiments, each mirror is optically associated with a respective lens (670a,b,c), such as a mini- or micro-lens, for the delivery and collection of light towards and from the skin sub-area. Other features may be similar to those described in FIG. 5.

Figure 7:
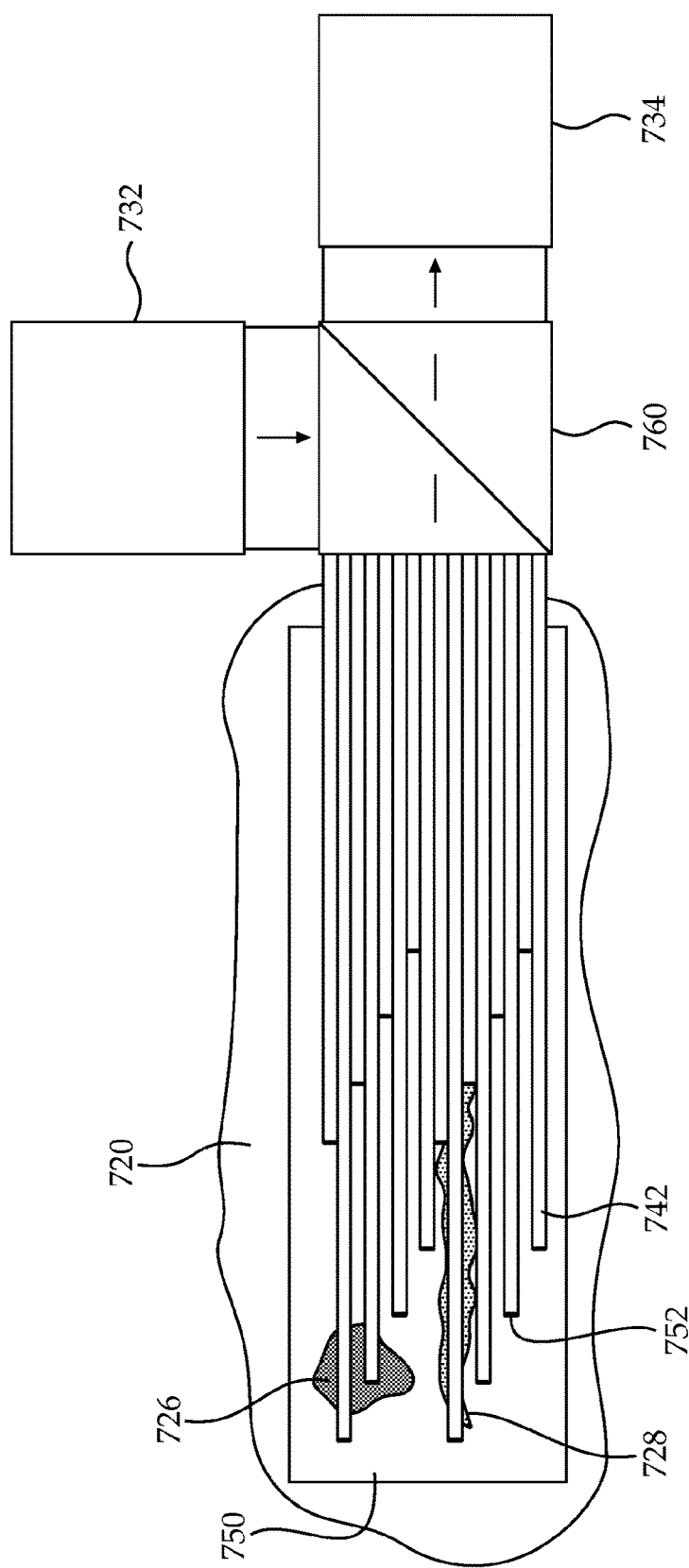
FIG. 7 schematically depicts a configuration of components within a device for detection of internal bleeding according to an exemplary embodiment of the current invention.

Reference is now made to FIG. 7, which illustrates detection of blood accumulated post-operatively in an area next to a surgical wound area, for example, a few centimeters (cm) from the surgical wound area, using a configuration of components similar to that depicted in FIG. 6. The figure schematically depicts a top view of a configuration of components within a device for detection of bleeding using a waveguide assembly (750), according to some exemplary embodiments of the current invention. Further shown is a body part (720) to be scanned for the presence of bleeding or hematoma, which contains a surgical wound area (728) and a hematoma area (726). The illustrated configuration includes a light source (732), a light detector (734) and a waveguide (750) divided to a plurality of optical channels (742). The illustrated configuration further includes a beam splitter (760) functionally disposed between the waveguide assembly, and the light source and detector. The beam splitter is configured to deliver light from the light source to the waveguide assembly, and to deliver light from the waveguide assembly to the light detector. The illustrated waveguide assembly comprises a plurality of optical channels, each optical channel is configured to deliver light to and from a sub-area within a skin area of the patient. The waveguide comprises reflective elements, such as mirrors (752). The mirrors are arranged such that they are spatially separated across the waveguide. In the illustrated embodiment, an array of mirrors one next to the other is disposed in the waveguide, where the mirrors are arranged at different distances from the point in which light from the beam splitter enters the waveguide. In some embodiments, the mirrors are disposed at the same height, and form a planar configuration in the waveguide. In other embodiments, the mirrors are disposed at different heights in the waveguide. Each mirror is configured to receive light from the beam splitter and deflect light towards a sub-area within an area of a skin of the patient, and into an internal part of the body of the patient. Each mirror is further configured to receive light from that sub-area and deflect the light towards the beam splitter. The spatial division of the mirrors within the waveguide creates a plurality of optical channels that are spatially distinct thus allowing spatial resolution of the signals delivered and collected from the skin area covered. In some embodiments, each mirror is optically associated with a respective lens, such as a mini- or micro-lens (not shown in the figure), for the delivery and collection of light towards and from the skin sub-area.

In some embodiments, the waveguide assembly further comprises a plurality of optic fibers, each is configured to deliver light to and from a sub-area within the skin area. In some embodiments, an array of optic fibers is used, where the fibers are spatially separated to maintain spatial resolution of the delivered and collected signals. For example, an array of optic fibers one next to the other may be disposed within the waveguide, as shown in the figure. The plurality of fibers collectively covers an area of the skin of the subject surrounding a surgical wound. Each optic fiber may be optically associated with a respective mirror and optionally with a respective lens, to direct light towards a sub-area within the skin area, and collect light from the sub-area. Each fiber and respective mirror and lens are configured to deliver light to and from a sub-area within the skin area, thus allowing spatial resolution of the signals delivered and collected from the skin area covered. Spatial resolution of the signals is maintained both when the signals are delivered to the skin and when collected from the skin. In the illustrated embodiment, the fibers (742) are of varying lengths. In other embodiments, the fibers may be of the same length. In the illustrated embodiments, the fibers are disposed at the same height, and form a planar configuration in the waveguide. In other embodiments, the fibers may be disposed at different heights in the waveguide.

Differences between the parameters measured from the optical channels corresponding to the bleeding sub-areas and the parameters measured from the optical channels corresponding to other sub-areas are analyzed by a processor (not shown in the figure), which is configured to provide an indication of the existence of bleeding based on the analysis, and optionally provide an indication of the bleeding location.

According to some embodiments, implementation of the waveguide may be based on materials such as plastic or silicone and in particular based on photonic band gap crystals.

Figure 8A:
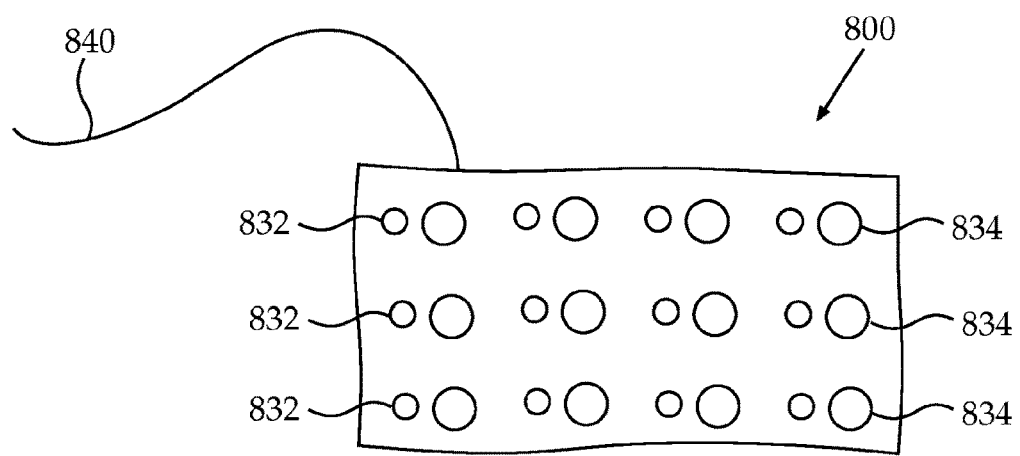
FIGS. 8A-8B schematically depict an optical interface according to exemplary embodiments of the current invention.

Reference is now made to FIG. 8A, which schematically depicts an optical interface (800) according to some embodiments. The illustrated optical interface comprises an array of IR light sources (832) configured to transmit IR light directly through the skin into an internal layer of a body, and an array of adjacent IR light detectors (834) configured to detect IR light reflected from the body. According to some embodiments lenses, optically associated with the IR sourced, may be used for focusing the transmitted light into the internal layers (not shown in the figure). Alternatively or additionally, lenses, optically associated with the IR detectors, may be used enhancing collecting efficiency of reflected IR light.

Figure 8B:
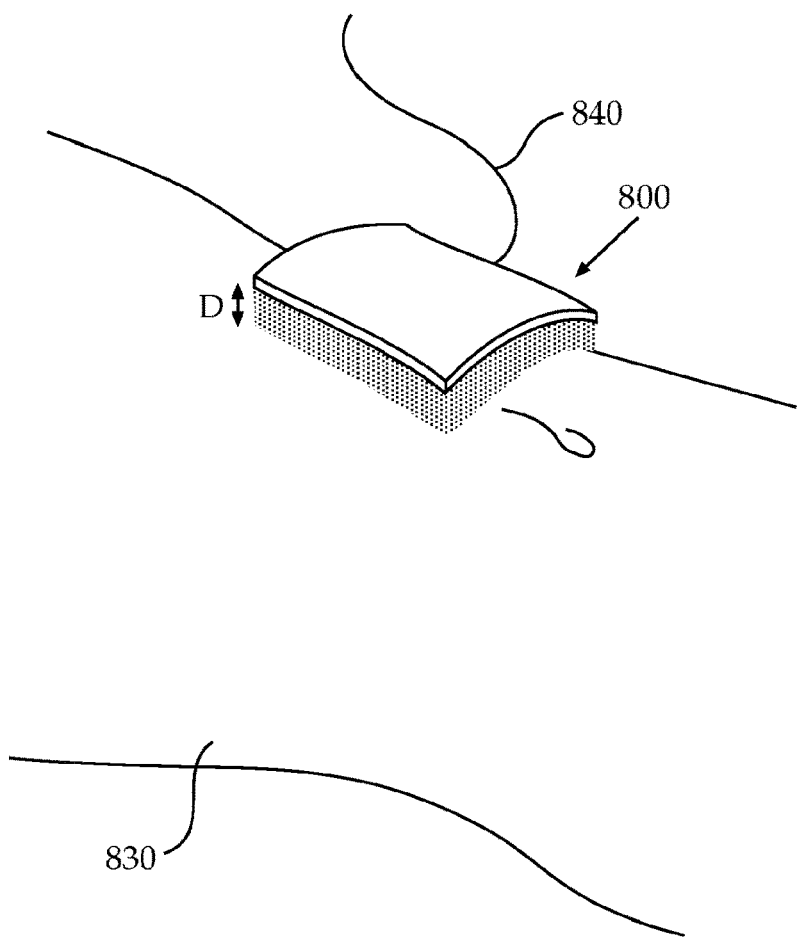

Reference is now made to FIG. 8B, which schematically depicts the optical interface (800) attached to a body (830) for detecting an internal bleeding therein. The optical interface is disposed so that the array of light sources and the array of light detectors do not substantially contact the skin and are substantially arranged at a small distance D from the skin. Thus, each light source generates an illuminated sub-area on the skin, defined by the cross-section of the light beam of the light source at the distance of the skin from the light source. Further, the detector may efficiently collect IR light which is reflected from the illuminated regions, and particularly from internal layers of the body, substantially underneath the sub-area illuminated by the respective adjacent light source. The optical interface may functionally communicate e.g. using electrical wires (840), or wirelessly, with a signal processing module housed in a housing situated near the patient. According to some embodiments the transmitted IR light comprises wavelengths absorbed substantially exclusively by blood, and further comprises wavelengths not absorbed substantially exclusively by blood. IR light at wavelengths which are not absorbed substantially exclusively by blood may be used as a reference signal as is described in detail hereinabove, thereby rendering unnecessary an additional reference signal source, reference signal detector and reference signal interface unit. According to some embodiments, the optical interface further comprises the signal processing module. According to some embodiments, the optical interface may be used as a stand-alone, easily portable device (requiring only power supply, either from an external source such a wall outlet or from a portable power source such as a battery), for detecting internal bleeding in a patient's body.

Figure 9:
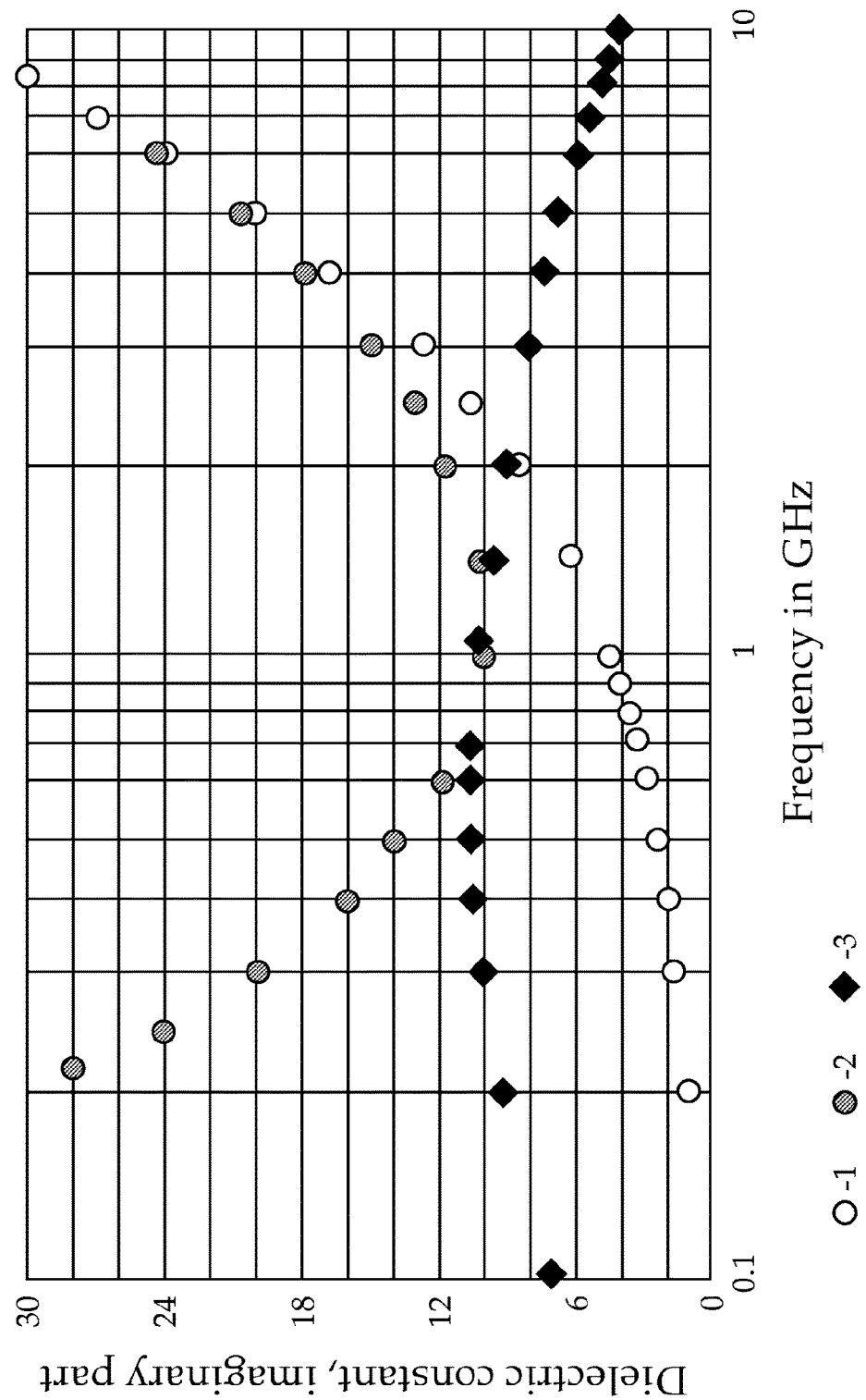
FIG. 9 shows frequency dependence of the imaginary part of the dielectric constant for free and bound water. 1—free water (salinity S=0 o/oo); 2—free water (salinity S=2 o/oo); 3—bound water.

In some embodiments there is use of RF radiation as a reference signal to detect changes in dielectric characteristics which are typically due to changes in the water content in the area of interest. RF radiation in the range of about 100 MHz to about 10 GHz may be used. Biological tissues are known to enable significant RF penetration. Changes in dielectric characteristics include the imaginary part of the dielectric constant. FIG. 9 illustrates the sensitivity of the dielectric constant to water and compares frequency dependence of the imaginary part of the dielectric constant for free and bound water. "1" represents free water (salinity S=0‰); "2" represents free water (salinity S=2‰); and "3" represents bound water. It is appreciated that a substantially minute variation in water characteristics (e.g. 2‰ salinity) generates such a different absorption spectrum e.g. between 0.1-1 GHz. Subsequently, RF signal may be used, at a selected wavelength, as a reference signal, having a similar absorption spectrum in blood and in other fluids known to accumulate in the body following a surgical intervention.

Figure 10A:
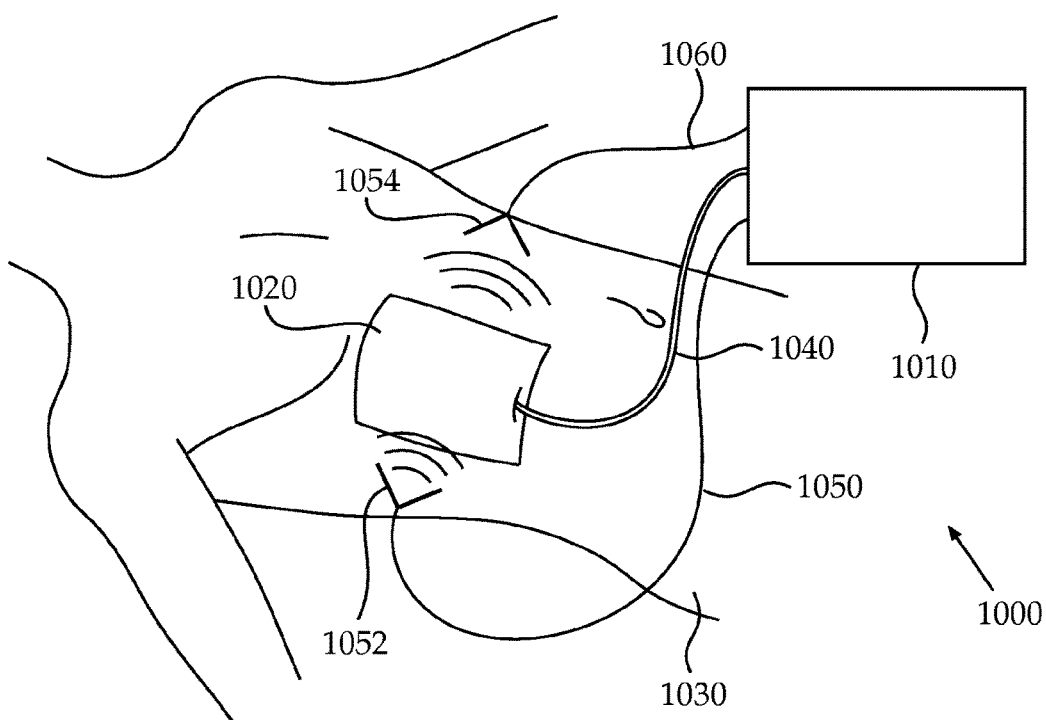
FIGS. 10A-10B schematically depict devices for detecting internal bleeding whereas the reference signal is RF radiation according to exemplary embodiments of the current invention.
Figure 10B:
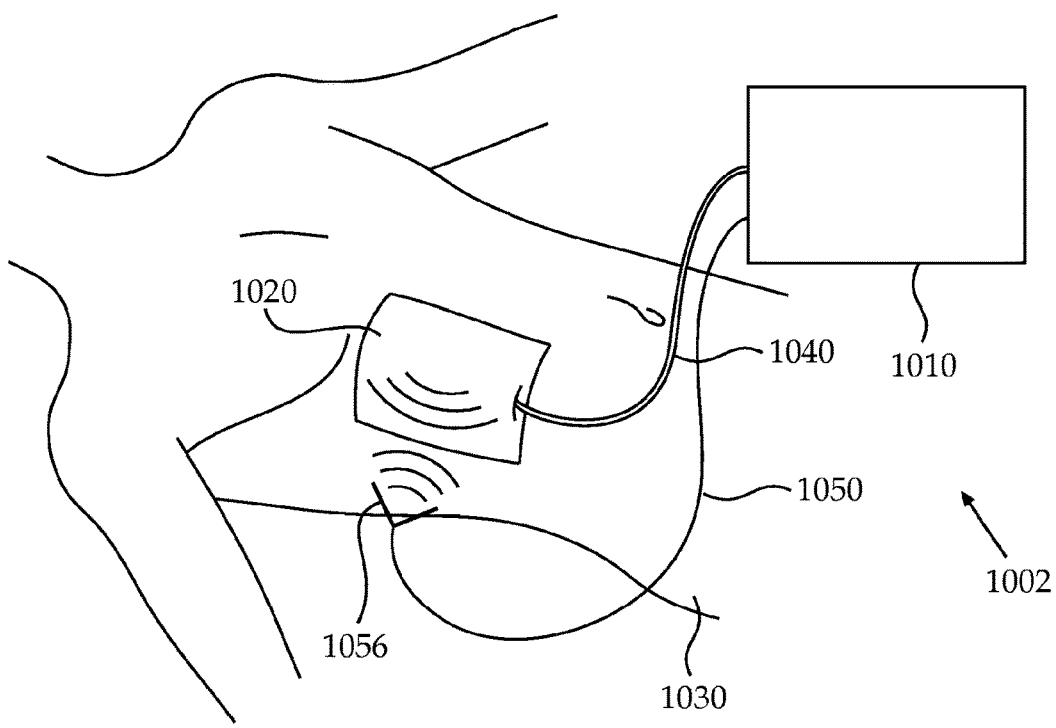

FIGS. 10A and 10B illustrate two embodiments of devices (1000, 1002) for detecting internal bleeding whereas the reference signal is RF radiation having a wavelength corresponding to a frequency in the range of 0.1-10 GHz. An optical interface (1020) comprising an adhesive pad is attached to a patient's body (1030). The optical interface comprises a delivery component configured to transmit IR light through the skin of the patient to an internal layer of the body, and a collecting component, as is described and detailed above (not shown in the figure). A control unit (1010), comprising a user interface such as keyboard, mouse, display, switches and/or operating knobs is associated with the optical interface and allows a user to activate the device. The control unit may include in some embodiments IR light source, IR light detector and a signal processing module (all not shown in this figure). Additionally or alternatively, all or some of these components of the device are included in the optical interface unit.

The illustrated device in FIG. 10A further includes a transmitting antenna (1052), situated and configured to transmit an RF reference signal towards the area of the skin which is illuminated by the IR light, and towards the internal layer underneath the area. The device further includes a receiving antenna (1054) situated and configured to receive RF signal transmitted through the body, and/or scattered by the body, possibly following absorption by the internal layer. According to some embodiments, the transmitting antenna and the receiving antenna may be situated in a sequence of positions in a trial and error process of finding an optimized position. Additionally or alternatively, the antennas may be situated in a pre-defined sequence of positions, whereas each position allows for obtaining a reference signal associated with a particular area or internal layer under the skin area.

An RF reference signal source (not shown in this figure) generates the RF reference signal transmitted by the transmitting antenna. In some embodiments the RF source may be housed in the control unit, and an RF signal is delivered from the source to the transmitting antenna using the illustrated wired connection (1050) between them. In some embodiments the RF source is substantially attached to the transmitting antenna, in which embodiments the control unit supplies to the antenna power and control commands.

An RF reference signal detector (not shown in this figure) is functionally associated with the receiving antenna for detecting RF reference signal collected by the receiving antenna. In some embodiments the RF detector may be housed in the control unit, and a received RF signal is delivered from the receiving antenna to the reference signal detector using the illustrated wired connection (1060) between the receiving antenna and the control unit. In some embodiments the RF detector is substantially attached to the receiving antenna, in which embodiments the control unit supplies to the receiving antenna power and control commands.

According to some embodiments one of the transmitting antenna and the receiving antenna may be substantially integrated with the pad of the optical interface. In some embodiments both transmitting antenna and receiving antenna are integrated with the pad of the optical interface unit. In such embodiments the device may have appearance as illustrated in FIG. 1 above, wherein a control unit is connected to a pad attached to the body, substantially using a single cable (1040) between them.

The illustrated device may be used substantially as described above. The IR signal may be used to monitor internal accumulation of fluids in the monitored internal layer, and particularly accumulation of blood due to an internal bleeding event. The RF reference signal may be used to monitor liquids accumulated in the monitored internal layer. By normalizing or adjusting or compensating the detected IR signal according to the detected RF reference signal and according to the teachings herein above, detection of internal bleeding may be obtained. Further, by comparing such normalized measurement results over time, namely comparing normalized results obtained at t=T to normalized results obtained at a prior time t=0, according to the teachings herein above, variation in blood content in the internal layer may be detected.

FIG. 10B illustrates an embodiment of a device for detecting bleeding in an internal layer of the body. The illustrated device is different from the device of FIG. 10A in having only a single antenna (1056) instead of two antennas in FIG. 10A. The antenna of the illustrated device is both a transmitting antenna and a receiving antenna. The antenna is positioned and configured to transmit an RF reference signal towards the area of the skin illuminated by the IR light transmitted, and to receive an RF reference signal substantially backscattered from the internal layer towards the antenna. According to some embodiments the antenna may be substantially integrated with the pad of the optical interface (1020), as is described above in FIG. 13.

Figure 11A:
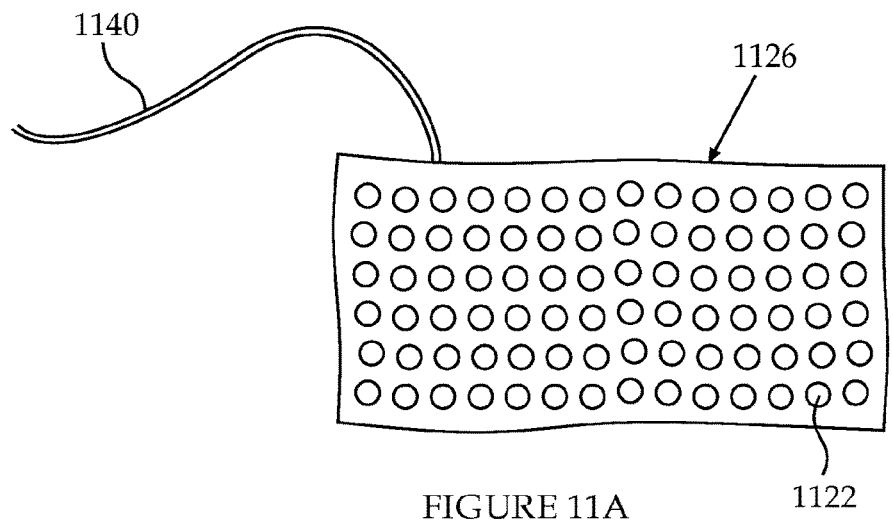
FIGS. 11A-11B schematically depict devices for detecting bleeding in an internal layer of the body, whereas the reference signal comprises an RF signal according to exemplary embodiments of the current invention.
Figure 11B:
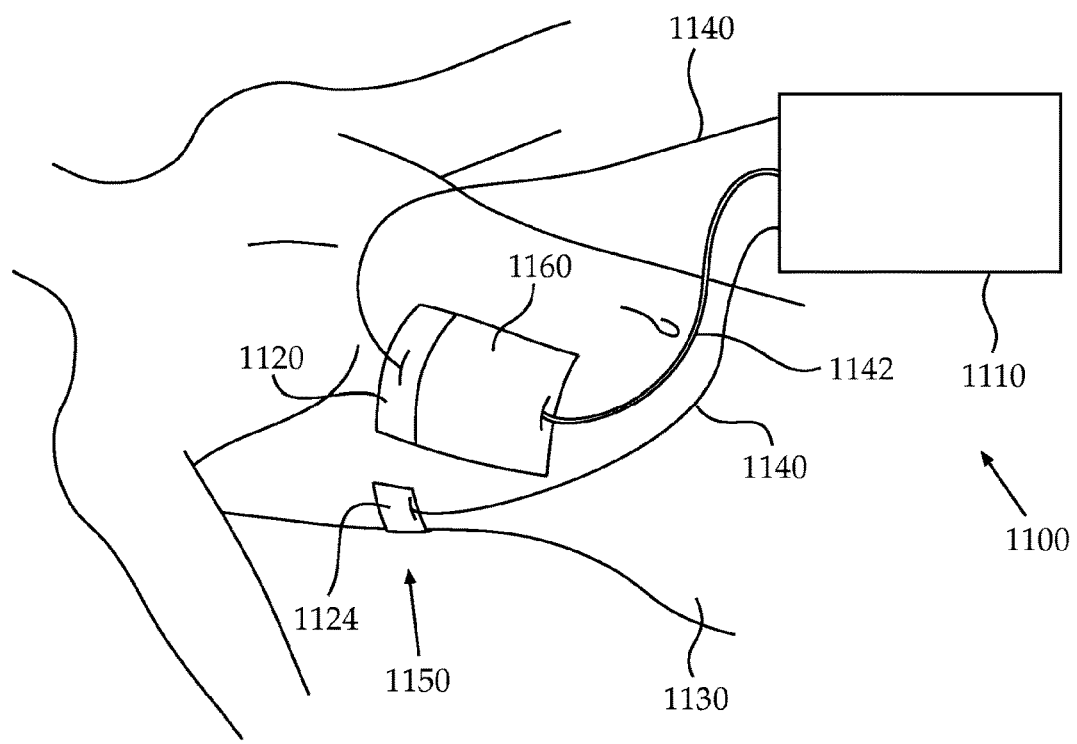

FIGS. 11A and 11B illustrate an embodiment of a device for detecting bleeding in an internal layer of the body, whereas the reference signal comprises an RF signal having a wavelength corresponding to a frequency in the range of 0.5-3 MHz. The illustrated device (1100) comprises a reference signal interface (1150) comprising a first electrical contact (1120) and a second electrical contact (1124). The first electrical contact is configured to be attached to the body on the area of the skin being illuminated by the IR light, or proximal thereto. The second electrical contact is configured to be attached to the body at a location different from that area of the skin. FIG. 11A schematically depicts an embodiment of an electrical contact such as the first electrical contact or the second electrical contact, according to some embodiments. The electrical contact comprises a pad (1126), possibly an adhesive pad, which is configured to attach to the skin, and an array of electrical contacts (1122), all being electrically connected together, and configured to touch the skin and assure good electrical contact with the skin. An electrical connection (1140) associates the electrical contact with the control unit. According to some embodiments the control unit includes an RF signal source which is configured to generate an RF reference signal, to be delivered to the body by the first electrical contact. According to some embodiments the control unit further comprises an RF reference signal detector, functionally associated with the second electrical contact, and configured to detect the RF signal received by the second electrical contact. According to some embodiments the RF signal generator, or the RF signal detector, or both, may be attached to the corresponding electrical contacts, respectively substantially as described above in FIG. 11A.

In use the RF reference signal in the described embodiment may generate an RF current passing through the patient's body substantially between the first electrical contact and the second electrical contact. It is appreciated that at the frequency range of 0.5 MHz to 3 MHz associated with the described embodiment the received reference signal is associated with RF voltage (between the first electrical contact and the second electrical contact) and with RF current contact (therebetween), rather than with radiation. The impedance of the body to RF signal in the specified frequency range is generally strongly affected by the contents of liquid in the body along the electrical path of the RF current. Thus, by measuring the RF voltage and RF current, and obtaining the body impedance therefrom, and possibly performing such measurements at several positions of the second electrical contact and/or of the first electrical contact, a mapping of the body impedance may be obtained. Subsequently, by mapping regions of a low impedance and regions of high impedance, regions in the body with high content of fluid may be identified. Further, by monitoring the time-variation of the received RF signal and the resultant RF impedance of the body when the first electrical contact and the second electrical contact are fixed in respective positions on the skin, a reference signal indicating the time variation fluid accumulated in the body may be obtained. Such time varying signal may further be used for normalizing and/or adjusting and/or compensating the IR signal measurement results, to obtain an efficient detection of internal bleeding in the body, as substantially described above.

Figure 12:
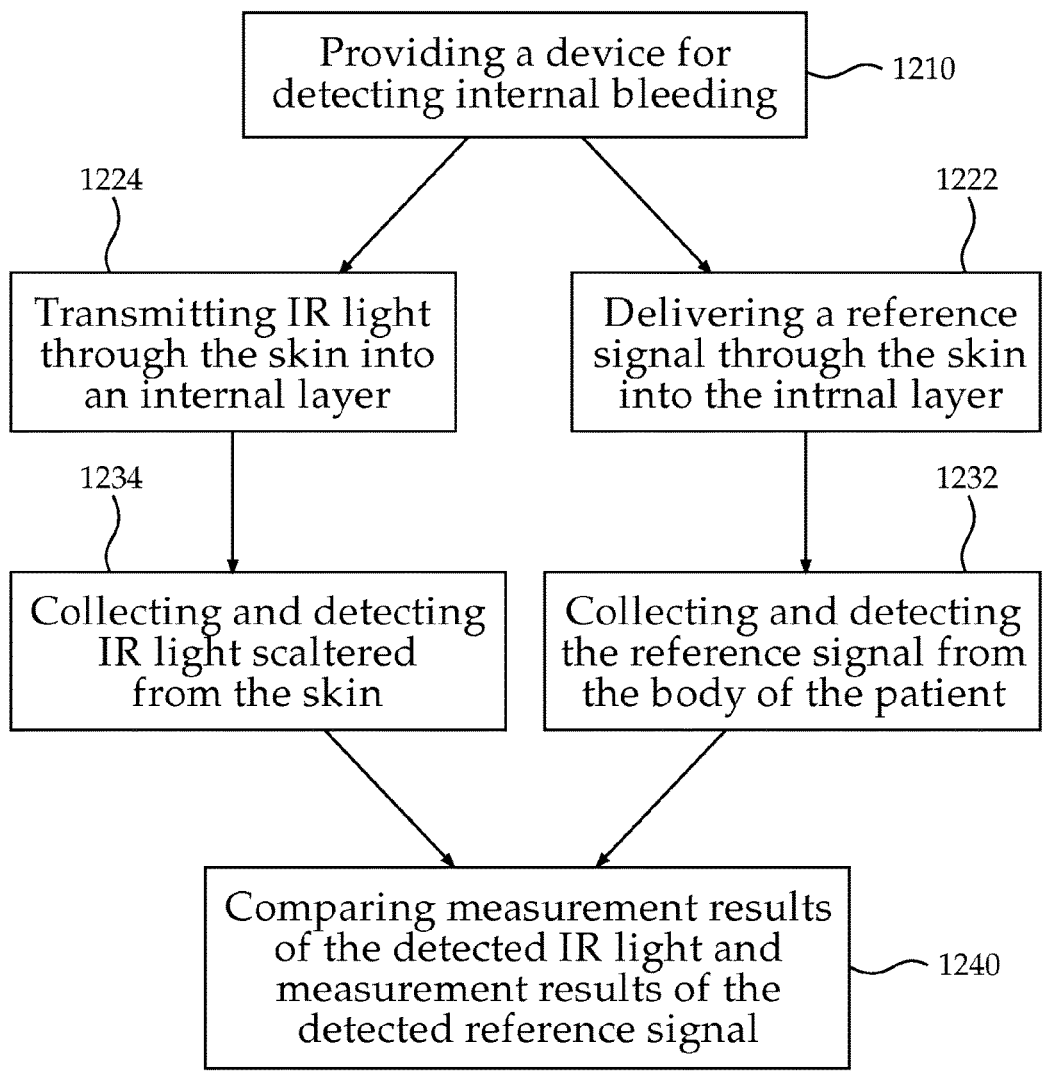
FIG. 12 schematically illustrates a method for detecting internal bleeding in a body of a patient according to an exemplary embodiment of the current invention.

FIG. 12 schematically illustrates an embodiment of a method for detecting internal bleeding in a body of a patient. The method comprises providing a device, for detecting internal bleeding substantially as described herein (1210); transmitting IR light through the skin into an internal layer (1224); delivering a reference signal through the skin into the internal layer (1222); collecting and detecting IR light scattered from the skin (1234); collecting and detecting the reference signal from the body of the patient (1232); and comparing measurement results of the detected IR light and measurement results of the detected reference signal (1240).

Figure 13:
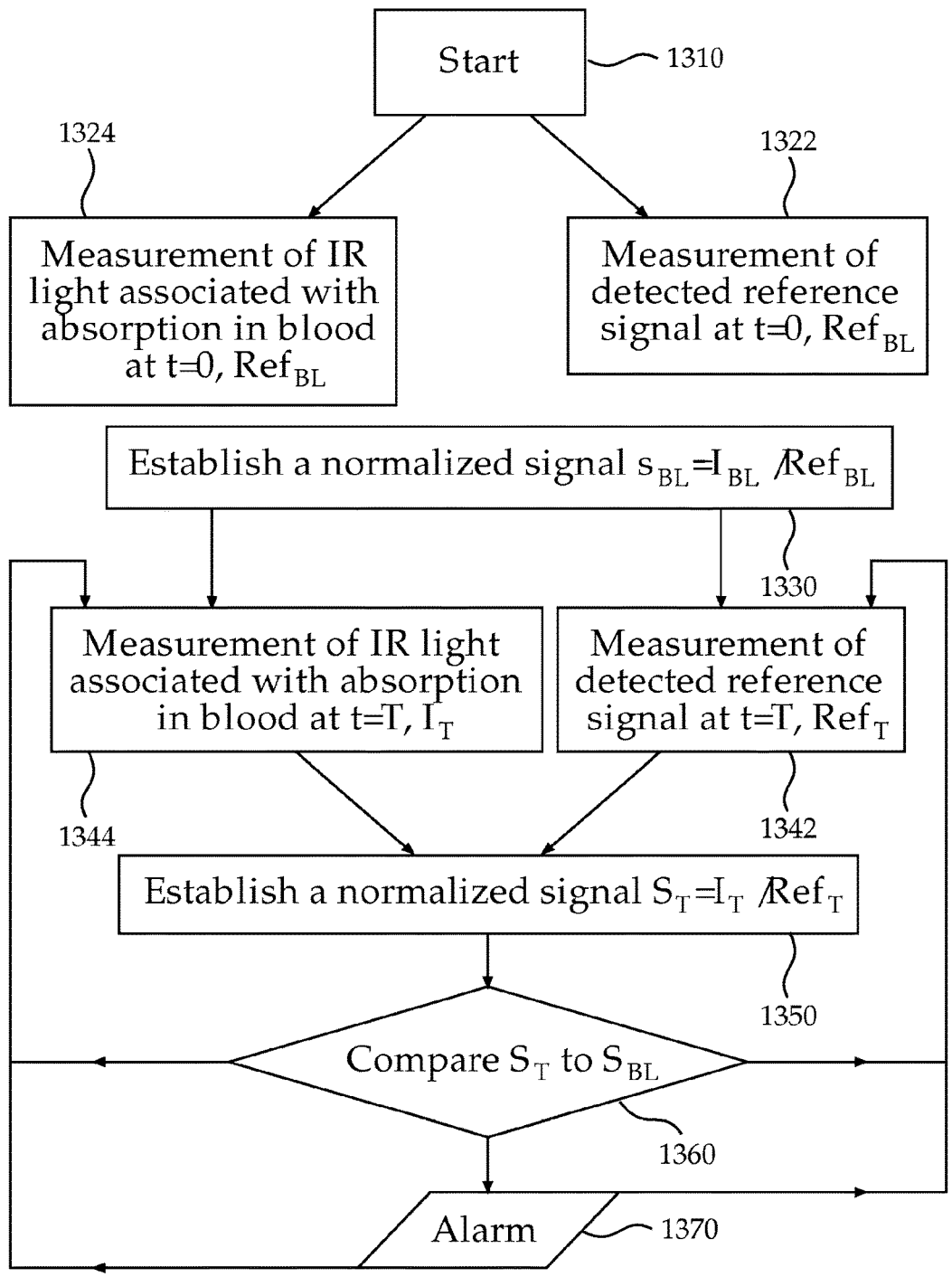
FIG. 13 schematically illustrates a method for detecting internal bleeding in a body of a patient according to an exemplary embodiment of the current invention.

FIG. 13 schematically illustrates another embodiment of a method for detecting internal bleeding in a body of a patient. The method comprises measuring detected IR light, $I_{BL}$, associated with absorption in blood, at first point in time t=0 (1324); measuring detected reference signal, $Ref_{BL}$, at t=0 (1322); establishing (calculating) a normalized signal $S_{BL}=I_{BL}/Ref_{BL}$ (1330); measuring detected IR light, $I_T$, associated with absorption in blood, at a later point in time t=T (1344); measuring detected reference signal, $Ref_T$, at t=T (1342); establishing (calculating) a normalized signal $S_T=I_T/Ref_T$ (1350); comparing $S_T$ to $S_{BL}$ (1360); if the comparison in the previous step indicates detection of bleeding, activating an alarm (1370); and returning to the steps of measuring detected IR light, $I_T$ and measuring detected reference signal, at yet a later point in time. According to some embodiments, if an alarm, indicating a detection of internal bleeding is activated, the rate at which subsequent measurements are performed, is increased.

According to an aspect of some embodiments there is provided a device (FIG. 2, 200) for detection of internal bleeding (226) in a patient's body (220). The device comprises an IR light source (232) configured to generate light in the Infra-Red (IR) spectral range and an IR light detector (234) configured to detect light in the Infra-Red (IR) spectral range. The device further comprises an optical interface (240) comprising one or more delivery component (246) and one or more collection component (248). The delivery component comprises at least one first optical channel (242a, 242b, 242c), and configured to deliver IR light generated by the IR light source and to transmit the IR light through an at least one respective first sub-area (222a, 222b, 222c), on an area (228) of a skin of the patient, into an internal layer of the body. The collection component comprises at least one second optical channel (244a, 244b, 244c), configured to collect IR light from an at least one respective second sub-area (224a, 224b, 224c), on the area of the skin, and to deliver the collected IR light to the IR light detector;

The device further comprises a reference signal source (238) configured to generate a reference signal, and a reference signal detector (236) configured to detect the reference signal. The device further comprises a reference signal interface (250) configured to deliver through the skin of the patient a reference signal from the reference signal source into the internal layer and to collect and deliver a collected reference signal to the reference signal detector.

The device further comprises a signal processing module (210) comprising a processor (202). The processor is configured to compare measurement results of IR light at a wavelength λ1, detected by the IR detector, to measurement results of reference signal at a wavelength λ2, detected by the reference signal detector, thereby detecting an internal bleeding (226) in a patient's body.

According to some embodiments at least one second optical channel comprises a plurality of second optical channels (244a, 244b, 244c), configured to collect IR light from a respective plurality of second sub-areas (224a, 224b, 224c), and deliver the collected IR light to the IR light detector. According to some embodiments at least one first optical channel comprises a plurality of first optical channels (242a, 242b, 242c) configured to deliver and to transmit IR light at a first respective plurality of first sub-areas (222a, 222b, 222c).

According to some embodiments the measurement results of the detected IR light comprise a measured parameter of the detected IR light selected from the group consisting of magnitude, amplitude, power, spectral line width, spectral content and spectral distribution of power. According to some embodiments the measurement results of the detected reference signal comprise a measured parameter of the detected reference signal selected from the group consisting of magnitude, amplitude, power, spectral line width, spectral content and spectral distribution of power.

According to some embodiments the measurement results of the detected IR light comprise a time dependent sequence of the measured parameter of the IR light. According to some embodiments the measurement results of the detected reference signal comprise a time dependent sequence of the measured parameter of the reference signal. According to some embodiments the processor is configured to detect an internal bleeding in a patient's body by analyzing time dependent sequences of measured parameters.

According to some embodiments the processor is configured to obtain, for each of the at least one second optical channels, a first measurement of an IR light parameter and of a reference signal parameter, $I_{BL}$ and $Ref_{BL}$, respectively, and at a later time a second measurement of the IR light parameter and of the reference signal parameter, $I_T$ and $Ref_T$, respectively and to compute a corresponding function $F(I_{BL}, Ref_{BL}, I_T, Ref_T)$. According to some embodiments the function is $I_{BL}/Ref_{BL}-I_T/Ref_T$. According to some embodiments the processor is configured to detect an internal bleeding (226) and a location thereof by identifying a sub-area (224) respective of an optical channel (244a) for which the function is equal to, or greater than or smaller than, a pre-determined threshold or a pre-determined value.

According to some embodiments the signal processing module is configured to controllably modulate the IR light generated by the IR light source so that the at least one first optical channel delivers modulated IR light. According to some embodiments the signal processing module is configured to modulate the collected IR light synchronously with the modulation of generated IR light.

According to some embodiments the reference signal comprises a Near IR (NIR) or a Mid IR (MIR) light or a Radio-Frequency (RF) signal. According to some embodiments the reference signal source is configured to generate a Radio-Frequency (RF) signal at a frequency in a range between about 0.1 to about 10 GHz. According to some embodiments the reference signal interface (250) comprises a transmitting RF antenna (FIG. 2, 252; FIG. 10A, 1052) for delivering the reference signal through the skin into the internal layer, and a receiving RF antenna (FIG. 2, 254; FIG. 10A, 1054) configured for collecting the reference signal. According to some embodiments the transmitting RF antenna comprises the receiving RF antenna (FIG. 10B, 1056).

According to some embodiments the reference signal source is configured to generate a Radio-Frequency (RF) signal at a frequency in a range between about 0.5 to about 3 MHz. According to some embodiments the reference signal interface (FIG. 11, 1150) comprises a first electrical contact (1120) configured to be attached to the area of the skin, and the reference signal interface further comprises a second electrical contact (1124) configured to be attached to the skin at a location different from the area. At least one of the first electrical contact and second electrical contact is functionally associated (1140) with the reference signal source for delivering the reference signal into the internal layer.

According to some embodiments the IR light comprises a Near IR (NIR) or a Mid IR (MIR) light. According to some embodiments the IR light consists of a substantially single spectral line having a wavelength about λ1. According to some embodiments the substantially single spectral line is an absorption line of hemoglobin. According to some embodiments λ1 is selected from the group consisting of 760 nm, 780 nm, 830 nm and 850 nm.

According to some embodiments the IR light comprises a wide-spectrum light having a spectral width selected from the group consisting of about 30 nm, 50, 100 nm and 200 nm within the IR spectral range. According to some embodiments the IR light comprises a Mid IR (MIR) light having a wavelength in a spectral range of 4-6 um.

According to some embodiments the collection component comprises the delivery component (FIG. 5, 540; FIG. 6, 640; FIG. 7, 750). According to some embodiments the second optical channel(s) (742) of the collection component (750) comprise the first optical channel(s) (742) of the delivery component. According to some embodiments the respective first sub-areas substantially overlap, respectively, with the respective second sub-areas (FIG. 3, 322a, 322b, 322c).

According to some embodiments the second optical channels (FIG. 2, 244a, 244b, 244c; FIG. 7, 742) of the collection component (248, 750) comprise optical fibers, respectively, configured to collect IR light from the respective second sub-areas (224a, 224b, 224c). According to some embodiments the first optical channels (FIG. 2, 242a, 242b, 242c; FIG. 7, 742) of the delivery component (246, 750) comprise optical fibers, respectively, configured to transmit the IR light through the respective first sub-areas (222a, 222b, 222c), into an internal layer of the body.

According to some embodiments the collection component (FIG. 5, 540) comprises at least one optical fiber (544a, 544b, 544c), configured to deliver the IR light generated by the IR light source (532), and also to deliver the collected IR light to the IR light detector (534). According to some embodiments the collection component (540) comprises at least one lens (570a, 570b, 570c) optically associated with the at least one optical fiber (544a, 544b, 544c) so that the IR light is transmitted and collected through the lens. According to some embodiments the lens is a mini-lens having a diameter between 100 um and 2 mm According to some embodiments the lens is a micro-lens having a diameter between 10 um and 100 um.

According to some embodiments the collection component (FIG. 5, 540) comprises a waveguide assembly (550) comprising a mirror (552a, 552b, 552c) configured to deflect light generated by the IR source (532), thereby transmitting the IR light onto the sub area. The mirror is further configured to deflect light reflected from the sub area, thereby collecting the reflected IR light to the waveguide assembly. According to some embodiments the waveguide assembly (550) comprises a plurality of mirrors (552a, 552b, 552c) spatially separated across the waveguide thereby being configured to transmit the IR light at a plurality of sub-areas, and to collect the reflected IR light from the sub-areas. According to some embodiments the waveguide assembly (550) comprises an array of optic fibers (544a, 544b, 554c) disposed in the waveguide assembly wherein each optic fiber is optically associated with one of the plurality of mirrors (552a, 552b, 552c) so that IR light generated by the IR light source is delivered by the optic fibers and deflected by the mirrors to each of the sub-areas, respectively, and IR light reflected from each of the sub-areas is deflected by the respective mirror into the associated optic fiber to be delivered to the IR detector (534).

According to some embodiments the plurality of second optical channels comprises the plurality of first optical channels (FIG. 3, 342a, 342b, 342c). According to some embodiments each of the plurality of second optical channels comprises an optical fiber. According to some embodiments the plurality of first sub-areas comprise the plurality of second sub-areas (322a, 322b, 322b).

According to some embodiments the plurality of second optical channels (FIG. 3, 342a, 342b, 342c) are substantially optically isolated from one another thereby being configured to deliver IR light collected from each of the plurality of respective second sub-areas (322a, 322b, 322b), independently from one another. According to some embodiments the measurement results of the detected IR light comprise a measured parameter of the light detected independently from each of the plurality of second optical channels. According to some embodiments the device further comprises a spatial light modulator (370b) functionally disposed between the collection component and the IR detector, and configured to controllably and selectively deliver IR light from each of the plurality of second optical channels to the IR detector.

According to some embodiments the IR detector comprises a spatial array of light detecting elements. According to some embodiments the IR detector is selected from the group consisting of CCD, CMOS sensor, Linear Contact Image Sensor (CIS), Two-Dimensional CIS and 3D image sensor.

According to some embodiments the device further comprises at least one beam splitter (FIG. 3, 360a, 360b, 360c; FIG. 5, 560; FIG. 6, 660; FIG. 7, 760) functionally disposed between the optical interface (340, 540, 640, 750) and the IR light source (332, 532, 632, 732) and the IR detector (334, 534, 634, 734). The beam splitter is configured to deliver IR light from the IR light source to the plurality of second optical channels and to deliver light from the plurality of second optical channels to the IR detector.

According to some embodiments the optical interface (FIG. 1, 120; FIGS. 10A and 10B, 1020, FIG. 11, 1120) is configured to be attached to the area of the skin. According to some embodiments the optical interface comprises an adhesive pad for attaching the optical interface to the area of the skin. According to some embodiments the adhesive pad is disposable.

According to an aspect of some embodiments there is provided an optical interface (FIG. 1, 120; FIG. 2, 240) for transmitting IR light through an area 228 of a skin of a patient and to collect IR light from the area of the skin. The optical interface is configured to be attached to the patient's body at the area of the skin or proximal thereto and comprises one or more delivery component (246) and one or more collection component (248). The delivery component comprises a plurality of first optical channels (242a, 242b, 242c) configured to transmit the IR light through a plurality of respective first sub-areas (222a, 222b, 222c), on the area of the skin, into an internal layer of the body. The collection component comprises a plurality of second optical channels (244a, 244b, 244c), configured to collect IR light from a plurality of respective second sub-areas (224a, 224b, 2242c) on the area of the skin.

According to some embodiments the plurality of first optical channels are configured to transmit the IR light so that the plurality of respective first sub-areas (222a, 222b, 222c) are substantially distinct from one another. According to some embodiments the plurality of second optical channels are configured to collect the IR light so that the plurality of respective second sub-areas (224a, 224b, 2242c) are substantially distinct from one another.

According to some embodiments the optical interface comprises an IR light source (FIG. 5, 532; FIG. 6, 632; FIG. 7, 732) functionally associated with the delivery component (540, 640, 740). According to some embodiments the optical interface (FIG. 8, 800) comprises a plurality of IR light sources (FIG. 8, 832), each associated with one of the plurality of first optical channels.

According to some embodiments the optical interface comprises an IR light detector (FIG. 5, 534; FIG. 6, 634; FIG. 7, 734) functionally associated with the collection component (540, 640, 740). According to some embodiments the optical interface (FIG. 8, 800) comprises a plurality of IR light detectors, each associated with one of the plurality of second optical channels.

According to some embodiments the collection component (FIG. 5, 540; FIG. 6, 640; FIG. 7, 740) comprises the delivery component so that each of the plurality of second optical channels is further configured to transmit the IR light through the respective second sub-areas on the area of the skin, into the internal layer of the body. According to some embodiments each of the optical channels comprises an optical fiber.

According to some embodiments the optical interface comprises a plurality of beam splitters (FIG. 3, 360a, 360b, 360c), each associated with one of the optical fibers (342a, 342b and 342c). According to some embodiments the optical interface comprises a plurality of IR light detectors, each associated with one of the plurality of beam splitters, and further comprising a plurality of IR light detectors, each associated with one of the plurality of beam splitters, so that each beam splitter is configured to deliver IR light from an IR light source substantially to the associated optical fiber, and to deliver IR light from the associated optical fiber substantially to an IR light detector.

According to some embodiments the optical interface comprises a plurality of lenses (FIG. 5, 570, FIG. 6, 670), each lens being optically associated with one of the plurality of first optical channels or second optical channels.

According to some embodiments the collection component comprises a waveguide assembly FIG. 5, 550; FIG. 6, 650; FIG. 7, 750). According to some embodiments the waveguide assembly comprises a plurality of mirrors (552, 652, 752), each associated with one of the optical channels and configured to deflect IR light of the optical channel to transmit the IR light through a respective sub-area, and to deflect IR light reflected from the respective sub-area thereby collecting the reflected IR light to the respective optical channel. According to some embodiments the optical interface comprises a plurality of lenses (FIG. 5, 570, FIG. 6, 670), each being optically associated with one of the plurality of mirrors (FIG. 5, 552, FIG. 6, 652) so that the IR light is transmitted and collected through the lens.

According to an aspect of some embodiments there is provided a method for detecting internal bleeding in a patient's body, comprising:

providing a device according to the teachings herein (FIG. 12, 1210);

transmitting IR light through a sub area of an area of a skin of the patient, into an internal layer of the body (1224);

collecting and detecting IR light scattered from a sub-area of the area of the skin (1234);

delivering a reference signal through the skin of the patient, into the internal layer of the body (1222);

collecting and detecting the reference signal from the body of the patient (1234), and comparing measurement results of the detected IR light and measurement results of the detected reference signal (1240).

According to an aspect of some embodiments there is provided a method for detecting internal bleeding in a patient's body, comprising:

measuring detected IR light, $I_{BL}$, associated with absorption in blood, at a first point in time t=0 (FIG. 13, 1324);

measuring detected reference signal, RefBL, at t=0 (1322);

establishing (calculating) a normalized signal $S_{BL}=I_{BL}/Ref_{BL}$ (1330);

measuring detected IR light, $I_T$, associated with absorption in blood, at a later point in time t=T (1344);

measuring detected reference signal, $Ref_T$, at t=T (1342);

establishing (calculating) a normalized signal $S_T=I_T/Ref_T$ (1350);

comparing $S_T$ to $S_{BL}$ (1360);

activating an alarm, if the comparison above indicates detection of bleeding (1370); and returning to the steps of measuring detected IR light, $I_T$, and measuring detected reference signal, $Ref_T$, at yet a later point in time (1342, 1344).

According to some embodiments the method further comprise increasing the rate at which subsequent measurements of detected IR light and detected reference signal are performed, if an alarm, indicating a detection of internal bleeding, is activated.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

REFERENCES

1. Bertand F O, Larose E et al. Outpatient Percutaneous Coronary Intervention: Ready for Prime Time?. Can J Cardiol 2007; 23(Suppl B):58B-66B.
2. Doyle B J, Rhial C S, et al. Bleeding, Blood Transfusion, and Increased Mortality After Percutaneous Coronary Intervention. JACC 2009; 53:2019-27.
3. Malvasi A, Tinelli A, et al. Subfascial Hematomas and Hemoperitoneum after Cesarean Section: Prevalence according to Closure and Non-Closure of the Parietal Peritoneum. Gynecol Obstet Invest 2008; 66:162-168.
4. Glaser M, Seigmuller M, et al. Prospective Study of the Incidence of Ultrasoud-Detected Hepatic Hematoma due to Percutaneous Menghini Needle Liver biopsy and Laparoscopy-Guided Silverman Needle Biopsy. Ital J Gastroenterol. 1994; 26(7):338-41.
5. McCrea H J, Ment L R, et al. The Diagnosis, Management, and Postnatal Prevention of Intraventricular Hemorrhage in the Preterm Neonate. Clin Perinatol. 2008; 35(4):777-92.

The invention claimed is:

1. A device for detection of internal bleeding in a patient's body, the device comprising:
    an IR light source configured to generate light in the Infra-Red (IR) spectral range;
    an IR light detector configured to detect light in the Infra-Red (IR) spectral range;
    an optical interface comprising
        at least one first optical channel configured to transmit IR light generated by said IR light source through an area of a skin of said patient, into an internal layer of the body, and
        one or more collection component, comprising at least one second optical channel, configured to collect reflected IR light from said area of said skin, and deliver said collected IR light to said IR light detector, and
    a reference signal source configured to generate a Radio-Frequency (RF) reference signal at a frequency of about 0.5 MHz-3 MHz,
    a reference signal detector configured to detect said reference signal,
    a reference signal interface configured to directly and independently from the IR source deliver through said area of the skin of the patient the reference signal from said reference signal source into said internal layer and to collect and deliver a collected reference signal to said reference signal detector, and
    a signal processing module comprising a processor configured to normalize measurement results of the detected IR light, detected by said IR detector, according to measurement results of the detected reference signal, detected by said reference signal detector, thereby detecting the internal bleeding in the patient's body.

2. The device of claim 1 wherein said measurement results of said detected IR light comprise a measured parameter of said detected IR light selected from the group consisting of spectral line width, spectral content and spectral distribution of power.

3. The device of claim 1 wherein said signal processing module is configured to controllably modulate said IR light generated by said IR light source so that said at least one first optical channel delivers modulated IR light, and to modulate said collected IR light synchronously with said modulation of said generated IR light.

4. The device of claim 1 wherein said reference signal interface comprises a first electrical contact configured to be attached to said area of the skin, and said reference signal interface further comprises a second electrical contact configured to be attached to the skin at a location different from said area, wherein at least one of said first electrical contact and second electrical contact is functionally associated with said reference signal source for delivering said reference signal into said internal layer.

5. The device of claim 1 wherein said generated IR light comprises a Mid IR (MIR) light having a wavelength in a spectral range of 4-6 um.

6. The device of claim 1 wherein said at least one second optical channel of said one or more collection component comprises said at least one first optical channel.

7. The device of claim 6 wherein said one or more collection component comprises at least one optical fiber, respectively, configured to deliver said IR light generated by said IR light source, and to also deliver said collected IR light to said IR light detector.

8. The device of claim 7 wherein said one or more collection component comprises at least one lens optically associated with said at least one optical fiber so that said transmitted IR light and said collected IR light pass through said lens, wherein said lens has a diameter between 10 um and 2 mm.

9. The device of claim 6 wherein said one or more collection component comprises a waveguide assembly comprising a plurality of mirrors spatially separated across the waveguide assembly thereby being configured to transmit said generated IR light to a plurality of sub-areas, and to collect said reflected IR light from said plurality of subareas.

10. The device of claim 9 wherein said waveguide assembly comprises an array of optic fibers disposed in said waveguide assembly wherein each optic fiber is optically associated with one of said plurality of mirrors so that said IR light generated by said IR light source is delivered by said optic fibers and deflected by a respective mirror to each of said plurality of sub-areas, respectively, and said IR light reflected from each of said sub-areas is deflected by said respective mirror into said associated optic fiber to be delivered to said IR detector.

11. The device of claim 1, wherein said optical interface comprises a disposable adhesive pad configured for attaching said optical interface to said area of the skin.

12. A method for detecting the internal bleeding in the patient's body, comprising: providing the device of claim 1; transmitting said transmitted IR light to the area of the skin of said patient, into the internal layer of the body; collecting and detecting the IR light reflected from the area of the skin; delivering the RF reference signal through the area of the skin of said patient, into the internal layer of the body; collecting and detecting the reference signal from the body of the patient, and normalizing the measurement results of the detected IR light according to the measurement results of the detected reference signal, thereby detecting the internal bleeding in the patient's body.

13. The method of claim 12 wherein said internal layer of the body of the patient is of one from the group consisting of a limb, abdominal cavity, chest cavity and digestive tract.

* * * * *